United States Patent [19]

Gaeta et al.

[11] Patent Number: 5,625,032

[45] Date of Patent: Apr. 29, 1997

[54] SELECTIVE AMYLIN ANTAGONIST PEPTIDES AND USES THEREFOR

[75] Inventors: Lori Gaeta, Olivenhain; Kevin Beaumont; Kathryn Prickett, both of San Diego, all of Calif.

[73] Assignee: Amylin Pharmaceuticals, Inc., San Diego, Calif.

[21] Appl. No.: 96,172

[22] Filed: Jul. 21, 1993

[51] Int. Cl.$^6$ ............................ A61K 38/16; C07K 14/00
[52] U.S. Cl. ...................... 530/324; 530/325; 530/326
[58] Field of Search ................................. 530/324, 325, 530/326; 514/12, 13

[56] References Cited

U.S. PATENT DOCUMENTS 5,260,275  11/1993  Cooper et al. ............................ 514/12

FOREIGN PATENT DOCUMENTS

| | | | |
|---|---|---|---|
| 0408294 | 1/1991 | European Pat. Off. | A61K 37/24 |
| 9310147 | 5/1993 | WIPO | C07K 7/10 |
| 9310146 | 5/1993 | WIPO | C07K 7/10 |

OTHER PUBLICATIONS

Patel, Biochem Soc. Trans., 17(5) 1989, p. 931.
McMartin, Biochem. Soc. Trans. 17(5) 1989, pp. 931–934.
Bundgaard et al., Biochem Soc. Trans., 17(5) 1989, pp. 947–949.
Morrison and Boyda, Organic Chemistry, 4th Ed., Allyn and Bacon, Inc., 1983, pp. 1117–1120.
U.S. Application Serial No. 07/794,288, filed Nov. 19, 1992, for "Novel Amylin Antagonist Peptides and Uses Therefor".
Amara, S.G. et al., *Science* 229:1094–1097 (1985).
Cooper, G.J.S. et al., *Proc. Natl. Acad. Sci. USA* 85:7763–7766 (1988).
Cooper, G.J.S. et al., *Proc. Natl. Acad. Sci. USA* 85:7763–7766 (1988).
Cooper, G.J.S. et al., *Biochem. Biophys. Acta.* 1014:247–258 (1989).
Cooper, G.J.S. et al., *Progress in Growth Factor Research* 1:99–105 (1989).

*Primary Examiner*—Christine M. Nucker
*Assistant Examiner*—Benet Prickril

[57] ABSTRACT

Peptides that inhibit amylin activity and that exhibit selectivity for amylin receptors relative to calcitonin and CGRP receptors are provided. These peptides may be used in the treatment of conditions where it is of benefit to reduce amylin activity, including the treatment of Type 2 diabetes mellitus, impaired glucose tolerance, obesity, insulin resistance and hypertension.

7 Claims, 13 Drawing Sheets

SEQUENCE LISTING ( 1 ) GENERAL INFORMATION:

( i i i ) NUMBER OF SEQUENCES: 40

( 2 ) INFORMATION FOR SEQ ID NO:1:

( i ) SEQUENCE CHARACTERISTICS:
        ( A ) LENGTH: 24 amino acids (B) TYPE: amino acid
            (D) TOPOLOGY: linear (ii) MOLECULE TYPE: peptide (ix) FEATURE:
            (A) NAME/KEY: Binding-site
            (B) LOCATION: 24
            (D) OTHER INFORMATION: /note= "Carboxy terminal amide"

(xi) SEQUENCE DESCRIPTION: SEQ ID NO:1:

Thr Gln Arg Leu Ala Asn Gln Leu Val Arg Leu Gln Thr Tyr Pro Arg
    1               5                   10                  15

Thr Asn Val Gly Ala Asn Thr Tyr
                20

(2) INFORMATION FOR SEQ ID NO:2:

(i) SEQUENCE CHARACTERISTICS:
            (A) LENGTH: 24 amino acids
            (B) TYPE: amino acid
            (D) TOPOLOGY: linear (ii) MOLECULE TYPE: peptide (ix) FEATURE:
            (A) NAME/KEY: Binding-site
            (B) LOCATION: 24
            (D) OTHER INFORMATION: /note= "Carboxy terminal amide"

(xi) SEQUENCE DESCRIPTION: SEQ ID NO:2:

Thr Gln Gln Leu Ala Asn Gln Leu Val Arg Leu Gln Thr Tyr Pro Arg
    1               5                   10                  15

Thr Asn Val Gly Ala Asn Thr Tyr
                20

(2) INFORMATION FOR SEQ ID NO:3:

(i) SEQUENCE CHARACTERISTICS:
            (A) LENGTH: 24 amino acids
            (B) TYPE: amino acid
            (D) TOPOLOGY: linear (ii) MOLECULE TYPE: peptide (ix) FEATURE:
            (A) NAME/KEY: Binding-site
            (B) LOCATION: 24
            (D) OTHER INFORMATION: /note= "Carboxy terminal amide"

(xi) SEQUENCE DESCRIPTION: SEQ ID NO:3:

Thr Gln Leu Leu Ala Asn Gln Leu Val Arg Leu Gln Thr Tyr Pro Arg
    1               5                   10                  15

Thr Asn Val Gly Ala Asn Thr Tyr
                20

(2) INFORMATION FOR SEQ ID NO:4:

(i) SEQUENCE CHARACTERISTICS:
            (A) LENGTH: 24 amino acids
            (B) TYPE: amino acid
            (D) TOPOLOGY: linear (ii) MOLECULE TYPE: peptide (ix) FEATURE:
            (A) NAME/KEY: Binding-site
            (B) LOCATION: 24
            (D) OTHER INFORMATION: /note= "Carboxy terminal amide"

(xi) SEQUENCE DESCRIPTION: SEQ ID NO:4:

```
Thr Gln Arg Leu Ala Asn Glu Leu Val Arg Leu Gln Thr Tyr Pro Arg
1               5                   10                  15

Thr Asn Val Gly Ala Asn Thr Tyr
                20
```

( 2 ) INFORMATION FOR SEQ ID NO:5:

( i ) SEQUENCE CHARACTERISTICS:
        ( A ) LENGTH: 24 amino acids
        ( B ) TYPE: amino acid
        ( D ) TOPOLOGY: linear ( i i ) MOLECULE TYPE: peptide ( i x ) FEATURE:
        ( A ) NAME/KEY: Binding-site
        ( B ) LOCATION: 24
        ( D ) OTHER INFORMATION: /note= "Carboxy terminal amide"

( x i ) SEQUENCE DESCRIPTION: SEQ ID NO:5:

```
Thr Gln Gln Leu Ala Asn Glu Leu Val Arg Leu Gln Thr Tyr Pro Arg
1               5                   10                  15

Thr Asn Val Gly Ala Asn Thr Tyr
                20
```

( 2 ) INFORMATION FOR SEQ ID NO:6:

( i ) SEQUENCE CHARACTERISTICS:
        ( A ) LENGTH: 24 amino acids
        ( B ) TYPE: amino acid
        ( D ) TOPOLOGY: linear ( i i ) MOLECULE TYPE: peptide ( i x ) FEATURE:
        ( A ) NAME/KEY: Binding-site
        ( B ) LOCATION: 24
        ( D ) OTHER INFORMATION: /note= "Carboxy terminal amide"

( x i ) SEQUENCE DESCRIPTION: SEQ ID NO:6:

```
Thr Gln Leu Leu Ala Asn Glu Leu Val Arg Leu Gln Thr Tyr Pro Arg
1               5                   10                  15

Thr Asn Val Gly Ala Asn Thr Tyr
                20
```

( 2 ) INFORMATION FOR SEQ ID NO:7:

( i ) SEQUENCE CHARACTERISTICS:
        ( A ) LENGTH: 24 amino acids
        ( B ) TYPE: amino acid
        ( D ) TOPOLOGY: linear ( i i ) MOLECULE TYPE: peptide ( i x ) FEATURE:
        ( A ) NAME/KEY: Binding-site
        ( B ) LOCATION: 24
        ( D ) OTHER INFORMATION: /note= "Carboxy terminal amide"

( x i ) SEQUENCE DESCRIPTION: SEQ ID NO:7:

```
Thr Gln Arg Leu Ala Asn Phe Leu Val Arg Leu Gln Thr Tyr Pro Arg
1               5                   10                  15

Thr Asn Val Gly Ala Asn Thr Tyr
                20
```

( 2 ) INFORMATION FOR SEQ ID NO:8:

( i ) SEQUENCE CHARACTERISTICS:

(A) LENGTH: 24 amino acids
(B) TYPE: amino acid
(D) TOPOLOGY: linear (ii) MOLECULE TYPE: peptide (ix) FEATURE:
(A) NAME/KEY: Binding-site
(B) LOCATION: 24
(D) OTHER INFORMATION: /note= "Carboxy terminal amide"

(xi) SEQUENCE DESCRIPTION: SEQ ID NO:8:

```
Thr Gln Gln Leu Ala Asn Phe Leu Val Arg Leu Gln Thr Tyr Pro Arg
1               5                   10                  15
Thr Asn Val Gly Ala Asn Thr Tyr
                20
```

(2) INFORMATION FOR SEQ ID NO:9:

(i) SEQUENCE CHARACTERISTICS:
(A) LENGTH: 24 amino acids
(B) TYPE: amino acid
(D) TOPOLOGY: linear (ii) MOLECULE TYPE: peptide (ix) FEATURE:
(A) NAME/KEY: Binding-site
(B) LOCATION: 24
(D) OTHER INFORMATION: /note= "Carboxy terminal amide"

(xi) SEQUENCE DESCRIPTION: SEQ ID NO:9:

```
Thr Gln Leu Leu Ala Asn Phe Leu Val Arg Leu Gln Thr Tyr Pro Arg
1               5                   10                  15
Thr Asn Val Gly Ala Asn Thr Tyr
                20
```

(2) INFORMATION FOR SEQ ID NO:10:

(i) SEQUENCE CHARACTERISTICS:
(A) LENGTH: 24 amino acids
(B) TYPE: amino acid
(D) TOPOLOGY: linear (ii) MOLECULE TYPE: peptide (ix) FEATURE:
(A) NAME/KEY: Binding-site
(B) LOCATION: 24
(D) OTHER INFORMATION: /note= "Carboxy terminal amide"

(xi) SEQUENCE DESCRIPTION: SEQ ID NO:10:

```
Thr Gln Arg Leu Ala Asn Gln Leu Val Arg Leu Gln Thr Tyr Pro Arg
1               5                   10                  15
Thr Asn Val Gly Ser Asn Thr Tyr
                20
```

(2) INFORMATION FOR SEQ ID NO:11:

(i) SEQUENCE CHARACTERISTICS:
(A) LENGTH: 24 amino acids
(B) TYPE: amino acid
(D) TOPOLOGY: linear (ii) MOLECULE TYPE: peptide (ix) FEATURE:
(A) NAME/KEY: Binding-site
(B) LOCATION: 24
(D) OTHER INFORMATION: /note= "Carboxy terminal amide"

( x i ) SEQUENCE DESCRIPTION: SEQ ID NO:11:

Thr Gln Gln Leu Ala Asn Gln Leu Val Arg Leu Gln Thr Tyr Pro Arg
1               5                   10                  15

Thr Asn Val Gly Ser Asn Thr Tyr
            20

( 2 ) INFORMATION FOR SEQ ID NO:12:

( i ) SEQUENCE CHARACTERISTICS:
        ( A ) LENGTH: 24 amino acids
        ( B ) TYPE: amino acid
        ( D ) TOPOLOGY: linear ( i i ) MOLECULE TYPE: peptide ( i x ) FEATURE:
        ( A ) NAME/KEY: Binding-site
        ( B ) LOCATION: 24
        ( D ) OTHER INFORMATION: /note= "Carboxy terminal amide"

( x i ) SEQUENCE DESCRIPTION: SEQ ID NO:12:

Thr Gln Leu Leu Ala Asn Gln Leu Val Arg Leu Gln Thr Tyr Pro Arg
1               5                   10                  15

Thr Asn Val Gly Ser Asn Thr Tyr
            20

( 2 ) INFORMATION FOR SEQ ID NO:13:

( i ) SEQUENCE CHARACTERISTICS:
        ( A ) LENGTH: 24 amino acids
        ( B ) TYPE: amino acid
        ( D ) TOPOLOGY: linear ( i i ) MOLECULE TYPE: peptide ( i x ) FEATURE:
        ( A ) NAME/KEY: Binding-site
        ( B ) LOCATION: 24
        ( D ) OTHER INFORMATION: /note= "Carboxy terminal amide"

( x i ) SEQUENCE DESCRIPTION: SEQ ID NO:13:

Thr Gln Arg Leu Ala Asn Glu Leu Val Arg Leu Gln Thr Tyr Pro Arg
1               5                   10                  15

Thr Asn Val Gly Ser Asn Thr Tyr
            20

( 2 ) INFORMATION FOR SEQ ID NO:14:

( i ) SEQUENCE CHARACTERISTICS:
        ( A ) LENGTH: 24 amino acids
        ( B ) TYPE: amino acid
        ( D ) TOPOLOGY: linear ( i i ) MOLECULE TYPE: peptide ( i x ) FEATURE:
        ( A ) NAME/KEY: Binding-site
        ( B ) LOCATION: 24
        ( D ) OTHER INFORMATION: /note= "Carboxy terminal amide"

( x i ) SEQUENCE DESCRIPTION: SEQ ID NO:14:

Thr Gln Gln Leu Ala Asn Glu Leu Val Arg Leu Gln Thr Tyr Pro Arg
1               5                   10                  15

Thr Asn Val Gly Ser Asn Thr Tyr
            20

( 2 ) INFORMATION FOR SEQ ID NO:15:

( i ) SEQUENCE CHARACTERISTICS:
    ( A ) LENGTH: 24 amino acids
    ( B ) TYPE: amino acid
    ( D ) TOPOLOGY: linear ( i i ) MOLECULE TYPE: peptide ( i x ) FEATURE:
    ( A ) NAME/KEY: Binding-site
    ( B ) LOCATION: 24
    ( D ) OTHER INFORMATION: /note= "Carboxy terminal amide"

( x i ) SEQUENCE DESCRIPTION: SEQ ID NO:15:

```
Thr Gln Leu Leu Ala Asn Glu Leu Val Arg Leu Gln Thr Tyr Pro Arg
1               5                   10                  15

Thr Asn Val Gly Ser Asn Thr Tyr
                20
```

( 2 ) INFORMATION FOR SEQ ID NO:16:

( i ) SEQUENCE CHARACTERISTICS:
        ( A ) LENGTH: 24 amino acids
        ( B ) TYPE: amino acid
        ( D ) TOPOLOGY: linear ( i i ) MOLECULE TYPE: peptide ( i x ) FEATURE:
        ( A ) NAME/KEY: Binding-site
        ( B ) LOCATION: 24
        ( D ) OTHER INFORMATION: /note= "Carboxy terminal amide"

( x i ) SEQUENCE DESCRIPTION: SEQ ID NO:16:

```
Thr Gln Arg Leu Ala Asn Phe Leu Val Arg Leu Gln Thr Tyr Pro Arg
1               5                   10                  15

Thr Asn Val Gly Ser Asn Thr Tyr
                20
```

( 2 ) INFORMATION FOR SEQ ID NO:17:

( i ) SEQUENCE CHARACTERISTICS:
        ( A ) LENGTH: 24 amino acids
        ( B ) TYPE: amino acid
        ( D ) TOPOLOGY: linear ( i i ) MOLECULE TYPE: peptide ( i x ) FEATURE:
        ( A ) NAME/KEY: Binding-site
        ( B ) LOCATION: 24
        ( D ) OTHER INFORMATION: /note= "Carboxy terminal amide"

( x i ) SEQUENCE DESCRIPTION: SEQ ID NO:17:

```
Thr Gln Gln Leu Ala Asn Phe Leu Val Arg Leu Gln Thr Tyr Pro Arg
1               5                   10                  15

Thr Asn Val Gly Ser Asn Thr Tyr
                20
```

( 2 ) INFORMATION FOR SEQ ID NO:18:

( i ) SEQUENCE CHARACTERISTICS:
        ( A ) LENGTH: 24 amino acids
        ( B ) TYPE: amino acid
        ( D ) TOPOLOGY: linear ( i i ) MOLECULE TYPE: peptide ( i x ) FEATURE:
        ( A ) NAME/KEY: Binding-site
        ( B ) LOCATION: 24
        ( D ) OTHER INFORMATION: /note= "Carboxy terminal amide"

( x i ) SEQUENCE DESCRIPTION: SEQ ID NO:18:

Thr Gln Leu Leu Ala Asn Phe Leu Val Arg Leu Gln Thr Tyr Pro Arg
1               5                   10                  15

Thr Asn Val Gly Ser Asn Thr Tyr
            20

( 2 ) INFORMATION FOR SEQ ID NO:19:

( i ) SEQUENCE CHARACTERISTICS:
        ( A ) LENGTH: 25 amino acids
        ( B ) TYPE: amino acid
        ( D ) TOPOLOGY: linear ( i i ) MOLECULE TYPE: peptide ( i x ) FEATURE:
        ( A ) NAME/KEY: Binding-site
        ( B ) LOCATION: 25
        ( D ) OTHER INFORMATION: /note= "Carboxy terminal amide"

( x i ) SEQUENCE DESCRIPTION: SEQ ID NO:19:

Ala Thr Gln Arg Leu Ala Asn Gln Leu Val Arg Leu Gln Thr Tyr Pro
1               5                   10                  15

Arg Thr Asn Val Gly Ala Asn Thr Tyr
            20                  25

( 2 ) INFORMATION FOR SEQ ID NO:20:

( i ) SEQUENCE CHARACTERISTICS:
        ( A ) LENGTH: 25 amino acids
        ( B ) TYPE: amino acid
        ( D ) TOPOLOGY: linear ( i i ) MOLECULE TYPE: peptide ( i x ) FEATURE:
        ( A ) NAME/KEY: Binding-site
        ( B ) LOCATION: 25
        ( D ) OTHER INFORMATION: /note= "Carboxy terminal amide"

( x i ) SEQUENCE DESCRIPTION: SEQ ID NO:20:

Ala Thr Gln Gln Leu Ala Asn Gln Leu Val Arg Leu Gln Thr Tyr Pro
1               5                   10                  15

Arg Thr Asn Val Gly Ala Asn Thr Tyr
            20                  25

( 2 ) INFORMATION FOR SEQ ID NO:21:

( i ) SEQUENCE CHARACTERISTICS:
        ( A ) LENGTH: 25 amino acids
        ( B ) TYPE: amino acid
        ( D ) TOPOLOGY: linear ( i i ) MOLECULE TYPE: peptide ( i x ) FEATURE:
        ( A ) NAME/KEY: Binding-site
        ( B ) LOCATION: 25
        ( D ) OTHER INFORMATION: /note= "Carboxy terminal amide"

( x i ) SEQUENCE DESCRIPTION: SEQ ID NO:21:

Ala Thr Gln Leu Leu Ala Asn Gln Leu Val Arg Leu Gln Thr Tyr Pro
1               5                   10                  15

Arg Thr Asn Val Gly Ala Asn Thr Tyr
            20                  25

( 2 ) INFORMATION FOR SEQ ID NO:22:

( i ) SEQUENCE CHARACTERISTICS:
    ( A ) LENGTH: 25 amino acids
    ( B ) TYPE: amino acid
    ( D ) TOPOLOGY: linear ( i i ) MOLECULE TYPE: peptide ( i x ) FEATURE:
    ( A ) NAME/KEY: Binding-site
    ( B ) LOCATION: 25
    ( D ) OTHER INFORMATION: /note= "Carboxy terminal amide"

( x i ) SEQUENCE DESCRIPTION: SEQ ID NO:22:

```
Ala Thr Gln Arg Leu Ala Asn Glu Leu Val Arg Leu Gln Thr Tyr Pro
 1           5                   10                  15
Arg Thr Asn Val Gly Ala Asn Thr Tyr
            20                  25
```

( 2 ) INFORMATION FOR SEQ ID NO:23:

( i ) SEQUENCE CHARACTERISTICS:
    ( A ) LENGTH: 25 amino acids
    ( B ) TYPE: amino acid
    ( D ) TOPOLOGY: linear ( i i ) MOLECULE TYPE: peptide ( i x ) FEATURE:
    ( A ) NAME/KEY: Binding-site
    ( B ) LOCATION: 25
    ( D ) OTHER INFORMATION: /note= "Carboxy terminal amide"

( x i ) SEQUENCE DESCRIPTION: SEQ ID NO:23:

```
Ala Thr Gln Gln Leu Ala Asn Glu Leu Val Arg Leu Gln Thr Tyr Pro
 1           5                   10                  15
Arg Thr Asn Val Gly Ala Asn Thr Tyr
            20                  25
```

( 2 ) INFORMATION FOR SEQ ID NO:24:

( i ) SEQUENCE CHARACTERISTICS:
    ( A ) LENGTH: 25 amino acids
    ( B ) TYPE: amino acid
    ( D ) TOPOLOGY: linear ( i i ) MOLECULE TYPE: peptide ( i x ) FEATURE:
    ( A ) NAME/KEY: Binding-site
    ( B ) LOCATION: 25
    ( D ) OTHER INFORMATION: /note= "Carboxy terminal amide"

( x i ) SEQUENCE DESCRIPTION: SEQ ID NO:24:

```
Ala Thr Gln Leu Leu Ala Asn Glu Leu Val Arg Leu Gln Thr Tyr Pro
 1           5                   10                  15
Arg Thr Asn Val Gly Ala Asn Thr Tyr
            20                  25
```

( 2 ) INFORMATION FOR SEQ ID NO:25:

( i ) SEQUENCE CHARACTERISTICS:
    ( A ) LENGTH: 25 amino acids
    ( B ) TYPE: amino acid
    ( D ) TOPOLOGY: linear ( i i ) MOLECULE TYPE: peptide ( i x ) FEATURE:
    ( A ) NAME/KEY: Binding-site
    ( B ) LOCATION: 25

(D) OTHER INFORMATION: /note= "Carboxy terminal amide"

(xi) SEQUENCE DESCRIPTION: SEQ ID NO:25:

Ala Thr Gln Arg Leu Ala Asn Phe Leu Val Arg Leu Gln Thr Tyr Pro
1               5                   10                  15

Arg Thr Asn Val Gly Ala Asn Thr Tyr
            20              25

(2) INFORMATION FOR SEQ ID NO:26:

(i) SEQUENCE CHARACTERISTICS:
        (A) LENGTH: 25 amino acids
        (B) TYPE: amino acid
        (D) TOPOLOGY: linear (ii) MOLECULE TYPE: peptide (ix) FEATURE:
        (A) NAME/KEY: Binding-site
        (B) LOCATION: 25
        (D) OTHER INFORMATION: /note= "Carboxy terminal amide"

(xi) SEQUENCE DESCRIPTION: SEQ ID NO:26:

Ala Thr Gln Gln Leu Ala Asn Phe Leu Val Arg Leu Gln Thr Tyr Pro
1               5                   10                  15

Arg Thr Asn Val Gly Ala Asn Thr Tyr
            20              25

(2) INFORMATION FOR SEQ ID NO:27:

(i) SEQUENCE CHARACTERISTICS:
        (A) LENGTH: 25 amino acids
        (B) TYPE: amino acid
        (D) TOPOLOGY: linear (ii) MOLECULE TYPE: peptide (ix) FEATURE:
        (A) NAME/KEY: Binding-site
        (B) LOCATION: 25
        (D) OTHER INFORMATION: /note= "Carboxy terminal amide"

(xi) SEQUENCE DESCRIPTION: SEQ ID NO:27:

Ala Thr Gln Leu Leu Ala Asn Phe Leu Val Arg Leu Gln Thr Tyr Pro
1               5                   10                  15

Arg Thr Asn Val Gly Ala Asn Thr Tyr
            20              25

(2) INFORMATION FOR SEQ ID NO:28:

(i) SEQUENCE CHARACTERISTICS:
        (A) LENGTH: 25 amino acids
        (B) TYPE: amino acid
        (D) TOPOLOGY: linear (ii) MOLECULE TYPE: peptide (ix) FEATURE:
        (A) NAME/KEY: Binding-site
        (B) LOCATION: 25
        (D) OTHER INFORMATION: /note= "Carboxy terminal amide"

(xi) SEQUENCE DESCRIPTION: SEQ ID NO:28:

Ala Thr Gln Arg Leu Ala Asn Gln Leu Val Arg Leu Gln Thr Tyr Pro
1               5                   10                  15

Arg Thr Asn Val Gly Ser Asn Thr Tyr
            20              25

( 2 ) INFORMATION FOR SEQ ID NO:29:

( i ) SEQUENCE CHARACTERISTICS:
        ( A ) LENGTH: 25 amino acids
        ( B ) TYPE: amino acid
        ( D ) TOPOLOGY: linear ( i i ) MOLECULE TYPE: peptide ( i x ) FEATURE:
        ( A ) NAME/KEY: Binding-site
        ( B ) LOCATION: 25
        ( D ) OTHER INFORMATION: /note= "Carboxy terminal amide"

( x i ) SEQUENCE DESCRIPTION: SEQ ID NO:29:

```
Ala  Thr  Gln  Gln  Leu  Ala  Asn  Gln  Leu  Val  Arg  Leu  Gln  Thr  Tyr  Pro
1                  5                            10                       15

Arg  Thr  Asn  Val  Gly  Ser  Asn  Thr  Tyr
              20                       25
```

( 2 ) INFORMATION FOR SEQ ID NO:30:

( i ) SEQUENCE CHARACTERISTICS:
        ( A ) LENGTH: 25 amino acids
        ( B ) TYPE: amino acid
        ( D ) TOPOLOGY: linear ( i i ) MOLECULE TYPE: peptide ( i x ) FEATURE:
        ( A ) NAME/KEY: Binding-site
        ( B ) LOCATION: 25
        ( D ) OTHER INFORMATION: /note= "Carboxy terminal amide"

( x i ) SEQUENCE DESCRIPTION: SEQ ID NO:30:

```
Ala  Thr  Gln  Leu  Leu  Ala  Asn  Gln  Leu  Val  Arg  Leu  Gln  Thr  Tyr  Pro
1                  5                            10                       15

Arg  Thr  Asn  Val  Gly  Ser  Asn  Thr  Tyr
              20                       25
```

( 2 ) INFORMATION FOR SEQ ID NO:31:

( i ) SEQUENCE CHARACTERISTICS:
        ( A ) LENGTH: 25 amino acids
        ( B ) TYPE: amino acid
        ( D ) TOPOLOGY: linear ( i i ) MOLECULE TYPE: peptide ( i x ) FEATURE:
        ( A ) NAME/KEY: Binding-site
        ( B ) LOCATION: 25
        ( D ) OTHER INFORMATION: /note= "Carboxy terminal amide"

( x i ) SEQUENCE DESCRIPTION: SEQ ID NO:31:

```
Ala  Thr  Gln  Arg  Leu  Ala  Asn  Glu  Leu  Val  Arg  Leu  Gln  Thr  Tyr  Pro
1                  5                            10                       15

Arg  Thr  Asn  Val  Gly  Ser  Asn  Thr  Tyr
              20                       25
```

( 2 ) INFORMATION FOR SEQ ID NO:32:

( i ) SEQUENCE CHARACTERISTICS:
        ( A ) LENGTH: 25 amino acids
        ( B ) TYPE: amino acid
        ( D ) TOPOLOGY: linear ( i i ) MOLECULE TYPE: peptide ( i x ) FEATURE:
        ( A ) NAME/KEY: Binding-site ( B ) LOCATION: 25
( D ) OTHER INFORMATION: /note= "Carboxy terminal amide"

( x i ) SEQUENCE DESCRIPTION: SEQ ID NO:32:

Ala Thr Gln Gln Leu Ala Asn Glu Leu Val Arg Leu Gln Thr Tyr Pro
1               5                   10                  15

Arg Thr Asn Val Gly Ser Asn Thr Tyr
            20                  25

( 2 ) INFORMATION FOR SEQ ID NO:33:

( i ) SEQUENCE CHARACTERISTICS:
    ( A ) LENGTH: 25 amino acids
    ( B ) TYPE: amino acid
    ( D ) TOPOLOGY: linear ( i i ) MOLECULE TYPE: peptide ( i x ) FEATURE:
    ( A ) NAME/KEY: Binding-site
    ( B ) LOCATION: 25
    ( D ) OTHER INFORMATION: /note= "Carboxy terminal amide"

( x i ) SEQUENCE DESCRIPTION: SEQ ID NO:33:

Ala Thr Gln Leu Leu Ala Asn Glu Leu Val Arg Leu Gln Thr Tyr Pro
1               5                   10                  15

Arg Thr Asn Val Gly Ser Asn Thr Tyr
            20                  25

( 2 ) INFORMATION FOR SEQ ID NO:34:

( i ) SEQUENCE CHARACTERISTICS:
    ( A ) LENGTH: 25 amino acids
    ( B ) TYPE: amino acid
    ( D ) TOPOLOGY: linear ( i i ) MOLECULE TYPE: peptide ( i x ) FEATURE:
    ( A ) NAME/KEY: Binding-site
    ( B ) LOCATION: 25
    ( D ) OTHER INFORMATION: /note= "Carboxy terminal amide"

( x i ) SEQUENCE DESCRIPTION: SEQ ID NO:34:

Ala Thr Gln Arg Leu Ala Asn Phe Leu Val Arg Leu Gln Thr Tyr Pro
1               5                   10                  15

Arg Thr Asn Val Gly Ser Asn Thr Tyr
            20                  25

( 2 ) INFORMATION FOR SEQ ID NO:35:

( i ) SEQUENCE CHARACTERISTICS:
    ( A ) LENGTH: 25 amino acids
    ( B ) TYPE: amino acid
    ( D ) TOPOLOGY: linear ( i i ) MOLECULE TYPE: peptide ( i x ) FEATURE:
    ( A ) NAME/KEY: Binding-site
    ( B ) LOCATION: 25
    ( D ) OTHER INFORMATION: /note= "Carboxy terminal amide"

( x i ) SEQUENCE DESCRIPTION: SEQ ID NO:35:

Ala Thr Gln Gln Leu Ala Asn Phe Leu Val Arg Leu Gln Thr Tyr Pro
1               5                   10                  15

Arg Thr Asn Val Gly Ser Asn Thr Tyr
            20                  25

( 2 ) INFORMATION FOR SEQ ID NO:36:

( i ) SEQUENCE CHARACTERISTICS:
        ( A ) LENGTH: 25 amino acids
        ( B ) TYPE: amino acid
        ( D ) TOPOLOGY: linear ( i i ) MOLECULE TYPE: peptide ( i x ) FEATURE:
        ( A ) NAME/KEY: Binding-site
        ( B ) LOCATION: 25
        ( D ) OTHER INFORMATION: /note= "Carboxy terminal amide"

( x i ) SEQUENCE DESCRIPTION: SEQ ID NO:36:

```
Ala  Thr  Gln  Leu  Leu  Ala  Asn  Phe  Leu  Val  Arg  Leu  Gln  Thr  Tyr  Pro
 1              5                        10                       15

Arg  Thr  Asn  Val  Gly  Ser  Asn  Thr  Tyr
             20                       25
```

( 2 ) INFORMATION FOR SEQ ID NO:37:

( i ) SEQUENCE CHARACTERISTICS:
        ( A ) LENGTH: 25 amino acids
        ( B ) TYPE: amino acid
        ( D ) TOPOLOGY: linear ( i i ) MOLECULE TYPE: peptide ( i x ) FEATURE:
        ( A ) NAME/KEY: Binding-site
        ( B ) LOCATION: 1
        ( D ) OTHER INFORMATION: /note= "Nitrogen terminal acetyl"

( i x ) FEATURE:
        ( A ) NAME/KEY: Binding-site
        ( B ) LOCATION: 25
        ( D ) OTHER INFORMATION: /note= "Carboxy terminal amide"

( x i ) SEQUENCE DESCRIPTION: SEQ ID NO:37:

```
Ala  Thr  Gln  Arg  Leu  Ala  Asn  Gln  Leu  Val  Arg  Leu  Gln  Thr  Tyr  Pro
 1              5                        10                       15

Arg  Thr  Asn  Val  Gly  Ser  Asn  Thr  Tyr
             20                       25
```

( 2 ) INFORMATION FOR SEQ ID NO:38:

( i ) SEQUENCE CHARACTERISTICS:
        ( A ) LENGTH: 25 amino acids
        ( B ) TYPE: amino acid
        ( D ) TOPOLOGY: linear ( i i ) MOLECULE TYPE: peptide ( i x ) FEATURE:
        ( A ) NAME/KEY: Binding-site
        ( B ) LOCATION: 1
        ( D ) OTHER INFORMATION: /note= "Nitrogen terminal acetyl"

( i x ) FEATURE:
        ( A ) NAME/KEY: Binding-site
        ( B ) LOCATION: 25
        ( D ) OTHER INFORMATION: /note= "Carboxy terminal amide"

( x i ) SEQUENCE DESCRIPTION: SEQ ID NO:38:

```
Ala  Thr  Gln  Leu  Leu  Ala  Asn  Glu  Leu  Val  Arg  Leu  Gln  Thr  Tyr  Pro
 1              5                        10                       15

Arg  Thr  Asn  Val  Gly  Ser  Asn  Thr  Tyr
             20                       25
```

(2) INFORMATION FOR SEQ ID NO:39:

(i) SEQUENCE CHARACTERISTICS:
        (A) LENGTH: 25 amino acids
        (B) TYPE: amino acid
        (D) TOPOLOGY: linear (ii) MOLECULE TYPE: peptide (ix) FEATURE:
        (A) NAME/KEY: Binding-site
        (B) LOCATION: 1
        (D) OTHER INFORMATION: /note= "Nitrogen terminal acetyl"

(ix) FEATURE:
        (A) NAME/KEY: Binding-site
        (B) LOCATION: 25
        (D) OTHER INFORMATION: /note= "Carboxy terminal amide"

(xi) SEQUENCE DESCRIPTION: SEQ ID NO:39:

```
Ala Thr Gln Gln Leu Ala Asn Glu Leu Val Arg Leu Gln Thr Tyr Pro
 1               5                  10                  15
Arg Thr Asn Val Gly Ser Asn Thr Tyr
                20                  25
```

(2) INFORMATION FOR SEQ ID NO:40:

(i) SEQUENCE CHARACTERISTICS:
        (A) LENGTH: 25 amino acids
        (B) TYPE: amino acid
        (D) TOPOLOGY: linear (ii) MOLECULE TYPE: peptide (ix) FEATURE:
        (A) NAME/KEY: Binding-site
        (B) LOCATION: 1
        (D) OTHER INFORMATION: /note= "Nitrogen terminal acetyl"

(ix) FEATURE:
        (A) NAME/KEY: Binding-site
        (B) LOCATION: 25
        (D) OTHER INFORMATION: /note= "Carboxy terminal amide"

(xi) SEQUENCE DESCRIPTION: SEQ ID NO:40:

```
Ala Thr Gln Arg Leu Ala Asn Glu Leu Val Arg Leu Gln Thr Tyr Pro
 1               5                  10                  15
Arg Thr Asn Val Gly Ser Asn Thr Tyr
                20                  25
```

SELECTIVE AMYLIN ANTAGONIST PEPTIDES AND USES THEREFOR

FIELD OF THE INVENTION

The present invention relates to peptides which inhibit amylin activity. These peptides may be used in the treatment of Type 2 diabetes mellitus and other disorders, including obesity, insulin resistance, impaired glucose tolerance, hypertension, disorders associated with renin secretion, and other disorders where amylin activity is beneficially reduced.

BACKGROUND OF THE INVENTION

Amylin is a recently discovered peptide which has marked effects on carbohydrate metabolism in vitro and in vivo, including the ability to inhibit the uptake of glucose and to suppress the synthesis of glycogen in isolated skeletal muscle. Cooper, G. J. S. et al., *Proc. Natl. Acad. Sci. USA* 85:7763–7766 (1988). A defect in amylin homeostasis is believed to contribute to insulin resistance and the development of Type 2 diabetes mellitus, Cooper, G. J. S. et al., *Biochim. Biophys. Acta.* 1014:247–258 (1989), as well as other metabolic disorders.

Amylin is a 37 amino acid peptide that shows about 46% identity in amino acid sequence on comparison with the calcitonin gene-related peptides (CGRPs). Cooper, G. J. S. et al., *Progress in Growth Factor Research* 1:99–105 (1989). CGRP shares limited sequence identity, about 30%, with calcitonin and common parentage in that alternate processing of a primary mRNA transcript leads to the generation of the two distinct peptides. Amara, S. G. et al., *Science* 229:1094–1097 (1985).

Compounds that inhibit the effects of amylin and its agonists (i.e., mimics of one or more of the effects of amylin) are referred to as amylin "antagonists." Amylin antagonist compounds and uses therefor are the subject of commonly owned U.S. application Ser. No. 07/794,288, filed Nov. 19, 1992, for "Novel Amylin Antagonist Peptides and Uses Therefor," the disclosure of which is hereby incorporated by reference.

Amylin antagonist peptides may or may not be selective for amylin receptors. More selective antagonists may exhibit less side effects than those which might be associated with more non-selective antagonists. For example, non-selective amylin antagonists may bind to calcitonin or CGRP receptors and could thereby produce unwanted effects related to calcium homeostasis or blood pressure regulation. It is an object of the invention to provide further novel and potent amylin antagonists, including antagonists which are more selective for amylin receptors than for calcitonin and CGRP receptors.

SUMMARY OF THE INVENTION

In one aspect, the invention provides novel compounds which are potent amylin antagonist peptides that are more selective for amylin receptors than calcitonin and CGRP receptors. Described and claimed are amylin antagonist peptides having the formula:

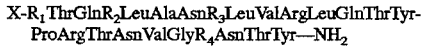

wherein $R_1$ is the amino acid residue Ala or a bond; $R_2$ is an amino acid residue selected from the group consisting of Arg, Gln, Lys, Asn and Leu; $R_3$ is an amino acid residue selected from the group consisting of Gln, Glu, Asn, Asp and Phe; $R_4$ is an amino acid residue selected from the group consisting of Ala and Ser; and X is hydrogen or an acetyl group. Additionally the valine residue at position 20 may be substituted for threonine, and the threonine residue at position 24 may be substituted for serine.

Also provided are preferred antagonists of the above formula, where:

$R_1$ is Ala, $R_2$ is Arg, $R_3$ is Glu, $R_4$ is Ser, and X is an acetyl group;

$R_1$ is Ala, $R_2$ is Arg, $R_3$ is Gln, $R_4$ is Ser, and X is an acetyl group;

$R_1$ is Ala, $R_2$ is Leu, $R_3$ is Glu, $R_4$ is Ser, and X is an acetyl group;

$R_1$ is Ala, $R_2$ is Gln, $R_3$ is Glu, $R_4$ is Ser, and X is an acetyl group;

$R_1$ is Ala, $R_2$ is Leu, $R_3$ is Gln, $R_4$ is Ser, and X is hydrogen; and, $R_1$ is Ala, $R_2$ is Gln, $R_3$ is Gln, $R_4$ is Ser, and X is hydrogen.

In another aspect, the invention provides pharmaceutical compositions comprising therapeutically effective amounts of the above amylin antagonist peptides and a pharmaceutically acceptable carrier, and methods of using these pharmaceutical compositions for the treatment of Type 2 diabetes mellitus and other disorders, including obesity, insulin resistance, impaired glucose tolerance, hypertension, disorders associated with renin secretion, and other disorders where amylin activity is beneficially reduced.

Other features and advantages of the invention will be apparent from the following detailed description of the invention and from the claims.

DETAILED DESCRIPTION OF THE INVENTION

PREFERRED PEPTIDES

Figure 1:
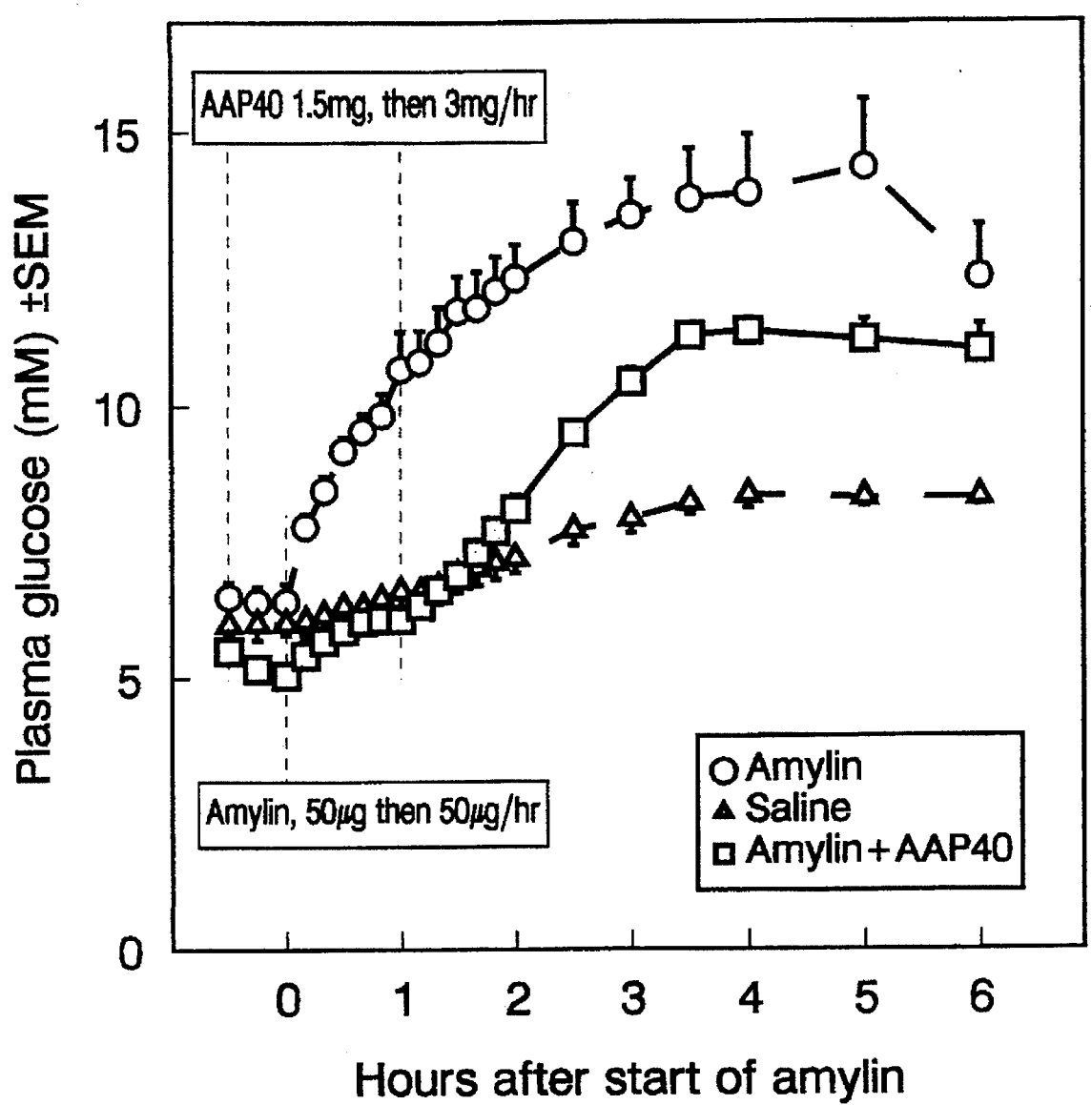
FIG. 1 illustrates the inhibition of amylin-induced hyperglycemia by prior infusion with AAP40 (SEQ ID NO:40). Plasma glucose (mM)±SEM is plotted as a function of hours after start of amylin. Test animals were infused with a 1.5 mg bolus of AAP40 (SEQ ID NO:40), followed by an infusion of 3 mg/hr for a further 1.5 hours. At t=0 hours (0.5 hours after the start of the AAP40 (SEQ ID NO:40) infusion) a 50 µg bolus of amylin was administered followed by an infusion of 50 µg/hour which continued until the end of the experiment. Squares indicate the response when amylin is administered in the presence of AAP40 (SEQ ID NO:40), circles, when amylin is administered alone, and triangles, when saline is administered instead of amylin.
Figure 2:
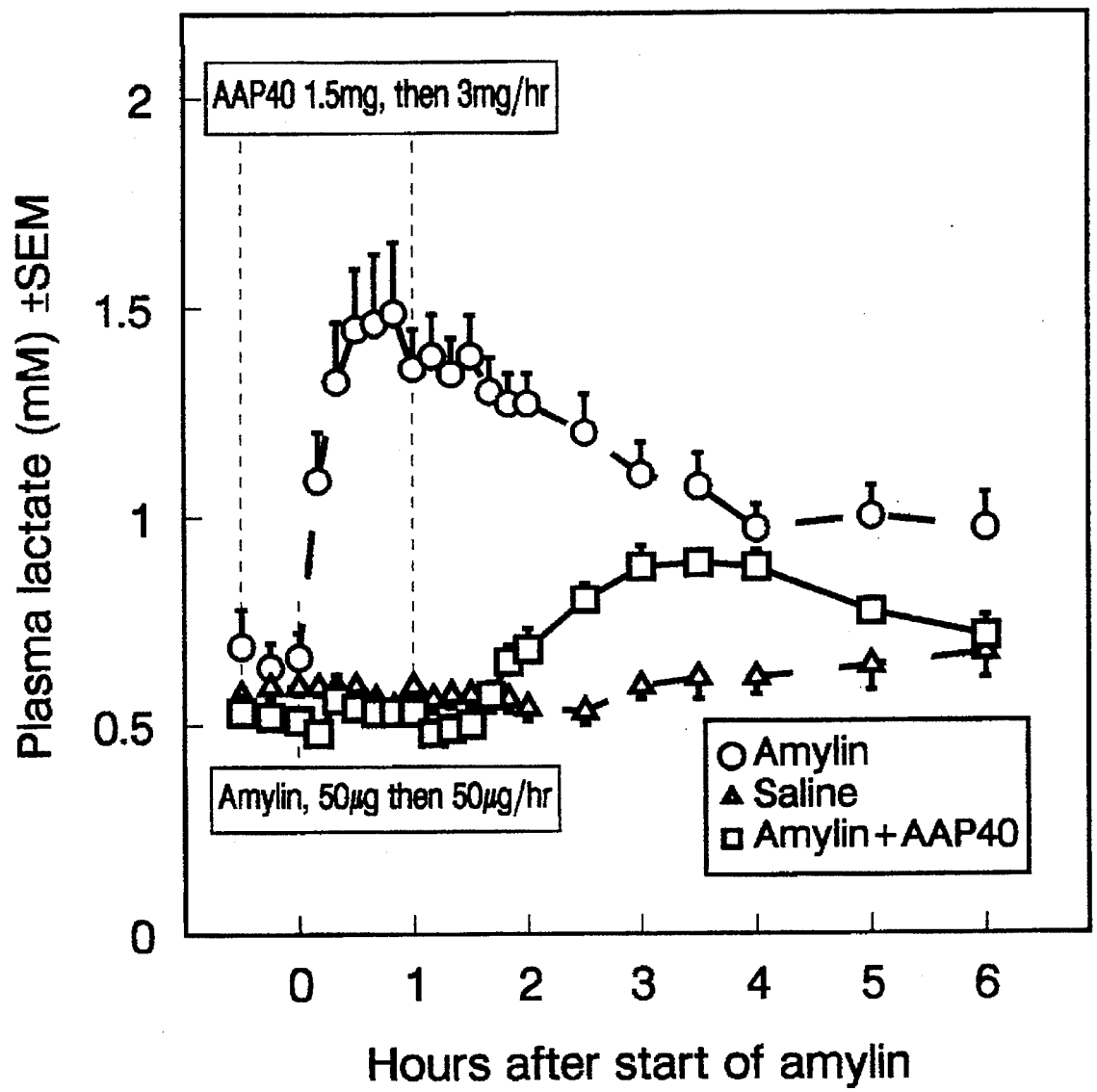
FIG. 2 illustrates the inhibition of amylin-induced hyperlactemia by prior infusion with AAP40 (SEQ ID NO:40). Plasma lactate (mM)±SEM is plotted as a function of hours after start of amylin. Test animals were infused with a 1.5 mg bolus of AAP40 (SEQ ID NO:40), followed by an infusion of 3 mg/hr for a further 1.5 hours. At t=0 hours (0.5 hours after the start of the AAP40 (SEQ ID NO:40) infusion) a 50 µg bolus of amylin was administered followed by an infusion of 50 µg/hour which continued until the end of the experiment. Squares indicate the response when amylin is administered in the presence of AAP40 (SEQ ID NO:40), circles, when amylin is administered alone, and triangles, when saline is administered instead of amylin.

The following is a detailed description of the amylin antagonist peptides of the invention. These peptides have the formula:

$$X\text{-}R_1\text{ThrGln}R_2\text{LeuAlaAsn}R_3\text{LeuValArgLeuGlnThrTyr-ProArgThrAsnValGly}R_4\text{AsnThrTyr}\text{—}NH_2$$

wherein $R_1$ is the amino acid residue Ala or a bond; $R_2$ is an amino acid residue selected from the group consisting of Arg, Gln, Lys, Asn and Leu; $R_3$ is an amino acid residue selected from the group consisting of Gln, Glu, Asn, Asp and Phe; $R_4$ is an amino acid residue selected from the group consisting of Ala and Ser; and X is hydrogen or an acetyl group.

Specific antagonists of the invention include the following:

| | |
|---|---|
| (SEQ ID NO: 1) (AAP1) | ThrGlnArgLeuAlaAsnGlnLeuValArgLeuGlnThrTyrProArgThrAsnValGlyAlaAsnThrTyr—NH$_2$; |
| (SEQ ID NO: 2) (AAP2) | ThrGlnGlnLeuAlaAsnGlnLeuValArgLeuGlnThrTyrProArgThrAsnValGlyAlaAsnThrTyr—NH$_2$; |
| (SEQ ID NO: 3) (AAP3) | ThrGlnLeuLeuAlaAsnGlnLeuValArgLeuGlnThrTyrProArgThrAsnValGlyAlaAsnThrTyr—NH$_2$; |
| (SEQ ID NO: 4) (AAP4) | ThrGlnArgLeuAlaAsnGluLeuValArgLeuGlnThrTyrProArgThrAsnValGlyAlaAsnThrTyr—NH$_2$; |
| (SEQ ID NO: 5) (AAP5) | ThrGlnGlnLeuAlaAsnGluLeuValArgLeuGlnThrTyrProArgThrAsnValGlyAlaAsnThrTyr—NH$_2$; |
| (SEQ ID NO: 6) (AAP6) | ThrGlnLeuLeuAlaAsnGluLeuValArgLeuGlnThrTyrProArgThrAsnValGlyAlaAsnThrTyr—NH$_2$; |
| (SEQ ID NO: 7) (AAP7) | ThrGlnArgLeuAlaAsnPheLeuValArgLeuGlnThrTyrProArgThrAsnValGlyAlaAsnThrTyr—NH$_2$; |
| (SEQ ID NO: 8) (AAP8) | ThrGlnGlnLeuAlaAsnPheLeuValArgLeuGlnThrTyrProArgThrAsnValGlyAlaAsnThrTyr—NH$_2$; |
| (SEQ ID NO: 9) (AAP9) | ThrGlnLeuLeuAlaAsnPheLeuValArgLeuGlnThrTyrProArgThrAsnValGlyAlaAsnThrTyr—NH$_2$; |
| (SEQ ID NO: 10) (AAP10) | ThrGlnArgLeuAlaAsnGlnLeuValArgLeuGlnThrTyrProArgThrAsnValGlySerAsnThrTyr—NH$_2$; |
| (SEQ ID NO: 11) (AAP11) | ThrGlnGlnLeuAlaAsnGlnLeuValArgLeuGlnThrTyrProArgThrAsnValGlySerAsnThrTyr—NH$_2$; |
| (SEQ ID NO: 12) (AAP12) | ThrGlnLeuLeuAlaAsnGlnLeuValArgLeuGlnThrTyrProArgThrAsnValGlySerAsnThrTyr—NH$_2$; |
| (SEQ ID NO: 13) (AAP13) | ThrGlnArgLeuAlaAsnGluLeuValArgLeuGlnThrTyrProArgThrAsnValGlySerAsnThrTyr—NH$_2$; |
| (SEQ ID NO: 14) (AAP14) | ThrGlnGlnLeuAlaAsnGluLeuValArgLeuGlnThrTyrProArgThrAsnValGlySerAsnThrTyr—NH$_2$; |
| (SEQ ID NO: 15) (AAP15) | ThrGlnLeuLeuAlaAsnGluLeuValArgLeuGlnThrTyrProArgThrAsnValGlySerAsnThrTyr—NH$_2$; |
| (SEQ ID NO: 16) (AAP16) | ThrGlnArgLeuAlaAsnPheLeuValArgLeuGlnThrTyrProArgThrAsnValGlySerAsnThrTyr—NH$_2$; |
| (SEQ ID NO: 17) (AAP17) | ThrGlnGlnLeuAlaAsnPheLeuValArgLeuGlnThrTyrProArgThrAsnValGlySerAsnThrTyr—NH$_2$; |
| (SEQ ID NO: 18) (AAP18) | ThrGlnLeuLeuAlaAsnPheLeuValArgLeuGlnThrTyrProArgThrAsnValGlySerAsnThrTyr—NH$_2$; |
| (SEQ ID NO: 19) (AAP19) | AlaThrGlnArgLeuAlaAsnGlnLeuValArgLeuGlnThrTyrProArgThrAsnValGlyAlaAsnThrTyr—NH$_2$; |
| (SEQ ID NO: 20) (AAP20) | AlaThrGlnGlnLeuAlaAsnGlnLeuValArgLeuGlnThrTyrProArgThrAsnValGlyAlaAsnThrTyr—NH$_2$; |
| (SEQ ID NO: 21) (AAP21) | AlaThrGlnLeuLeuAlaAsnGlnLeuValArgLeuGlnThrTyrProArgThrAsnValGlyAlaAsnThrTyr—NH$_2$; |
| (SEQ ID NO: 22) (AAP22) | AlaThrGlnArgLeuAlaAsnGluLeuValArgLeuGlnThrTyrProArgThrAsnValGlyAlaAsnThrTyr—NH$_2$; |

(SEQ ID NO: 23) (AAP23)  AlaThrGlnGlnLeuAlaAsnGluLeuValArgLeuGlnThrTyrProArgThrAsnValGlyAlaAsnThrTyr—NH$_2$;

(SEQ ID NO: 24) (AAP24)  AlaThrGlnLeuLeuAlaAsnGluLeuValArgLeuGlnThrTyrProArgThrAsnValGlyAlaAsnThrTyr—NH$_2$;

(SEQ ID NO: 25) (AAP25)  AlaThrGlnArgLeuAlaAsnPheLeuValArgLeuGlnThrTyrProArgThrAsnValGlyAlaAsnThrTyr—NH$_2$;

(SEQ ID NO: 26) (AAP26)  AlaThrGlnGlnLeuAlaAsnPheLeuValArgLeuGlnThrTyrProArgThrAsnValGlyAlaAsnThrTyr—NH$_2$;

(SEQ ID NO: 27) (AAP27)  AlaThrGlnLeuLeuAlaAsnPheLeuValArgLeuGlnThrTyrProArgThrAsnValGlyAlaAsnThrTyr—NH$_2$;

(SEQ ID NO: 28) (AAP28)  AlaThrGlnArgLeuAlaAsnGlnLeuValArgLeuGlnThrTyrProArgThrAsnValGlySerAsnThrTyr—NH$_2$;

(SEQ ID NO: 29) (AAP29)  AlaThrGlnGlnLeuAlaAsnGlnLeuValArgLeuGlnThrTyrProArgThrAsnValGlySerAsnThrTyr—NH$_2$;

(SEQ ID NO: 30) (AAP30)  AlaThrGlnLeuLeuAlaAsnGlnLeuValArgLeuGlnThrTyrProArgThrAsnValGlySerAsnThrTyr—NH$_2$;

(SEQ ID NO: 31) (AAP31)  AlaThrGlnArgLeuAlaAsnGluLeuValArgLeuGlnThrTyrProArgThrAsnValGlySerAsnThrTyr—NH$_2$;

(SEQ ID NO: 32) (AAP32)  AlaThrGlnGlnLeuAlaAsnGluLeuValArgLeuGlnThrTyrProArgThrAsnValGlySerAsnThrTyr—NH$_2$;

(SEQ ID NO: 33) (AAP33)  AlaThrGlnLeuLeuAlaAsnGluLeuValArgLeuGlnThrTyrProArgThrAsnValGlySerAsnThrTyr—NH$_2$;

(SEQ ID NO: 34) (AAP34)  AlaThrGlnArgLeuAlaAsnPheLeuValArgLeuGlnThrTyrProArgThrAsnValGlySerAsnThrTyr—NH$_2$;

(SEQ ID NO: 35) (AAP35)  AlaThrGlnGlnLeuAlaAsnPheLeuValArgLeuGlnThrTyrProArgThrAsnValGlySerAsnThrTyr—NH$_2$;

and (SEQ ID NO: 36) (AAP36)  AlaThrGlnLeuLeuAlaAsnPheLeuValArgLeuGlnThrTyrProArgThrAsnValGlySerAsnThrTyr—NH$_2$;

Antagonists of the invention may be non-acetylated at the N-terminus, as represented above, or acetylated.

Preferred antagonists include (SEQ ID NO:29) AAP 29 and AAP 30 (SEQ ID NO:30). Also preferred are:

(SEQ ID NO: 37) (AAP37)  acetyl-AlaThrGlnArgLeuAlaAsnGlnLeuValArgLeuGlnThrTyrProArgThrAsnValGlySerAsnThrTyr—NH$_2$;

(SEQ ID NO: 38) (AAP38)  acetyl-AlaThrGlnLeuLeuAlaAsnGluLeuValArgLeuGlnThrTyrProArgThrAsnValGlySerAsnThrTyr—NH$_2$;

(SEQ ID NO: 39) (AAP39)  acetyl-AlaThrGlnGlnLeuAlaAsnGluLeuValArgLeuGlnThrTyrProArgThrAsnValGlySerAsnThrTyr—NH$_2$;

Especially preferred is:

(SEQ ID NO:40) (AAP40) acetyl-AlaThrGlnArgLeuAlaAsnGluLeuValArgLeuGlnThrTyr-ProArgThrAsnValGlySerAsnThrTyr—NH$_2$.

ANTAGONIST ACTIVITY, SELECTIVITY AND POTENCY

The activity, selectivity and potency in vivo of amylin antagonists may be evaluated using certain biological assays described herein. The amylin receptor binding assay can be used to test for the binding and binding strength of both amylin agonists and antagonists. The soleus muscle assay can be used to test either amylin agonist or amylin antagonist activity in vitro. Other receptor binding assays can demonstrate the receptor selectivity of amylin antagonists. Infusion studies show, and can be used to verify the effects of amylin antagonists in vivo.

1. Amylin Receptor Binding Assay

The amylin receptor binding assay can be used to test the binding of amylin antagonist compounds. The amylin receptor binding assay is described in commonly owned International Application Number PCT/US92/02125, published Oct. 1, 1992, and titled "Receptor-Based Screening Methods for Amylin Agonists and Antagonists." The entire contents of this and other references cited herein are hereby incorporated by reference.

The amylin receptor binding assay is a competition assay which measures the ability of compounds to bind specifically to membrane-bound amylin receptors. A preferred source of the membrane preparations used in the assay is the rat basal forebrain which comprises membranes from the nucleus accumbens and surrounding regions. Compounds being assayed compete for binding to these receptor preparations with $^{125}$I Bolton Hunter rat amylin. Competition curves, wherein the amount bound (B) is plotted as a function of the log of the concentration of ligand, are analyzed by computer, using analyses by nonlinear regression to a 4-parameter logistic equation (Inplot program; GraphPAD Software, San Diego, Calif.).

As described in Example 7, peptides of the invention compete with amylin in the amylin receptor binding assay. In the amylin receptor binding assay, preferred peptides of the invention exhibit $IC_{50}$ values on the order of less than about 5 nanomolar (nM) and preferably less than about 1 nM.

2. Soleus Muscle Assay

Rat soleus muscle preparations have been in use for many years to study muscle glycogen metabolism and are well known in the field. The soleus muscle assay can be used to measure or test for amylin antagonist activity in vitro. Assays of biological activity of amylin or amylin antagonist preparations in the soleus muscle are performed using previously described methods (e.g., Young, A. A. et al., *Am. J. Physiol.* 263:E274–281 (1992)).

In summary, while amylin or amylin agonist activity is assessed by measuring the incorporation of radiolabelled glucose into glycogen in soleus muscle in response to an amylin or other amylin agonist, amylin antagonist activity is assessed by measuring the reversal of this inhibition in the presence of 100 nM rat amylin and an amylin antagonist. Concentrations of peptide dissolved in carrier-free buffers are determined by quantitative amino acid analysis, as described herein. The ability of compounds to act as antagonists in this assay can also be evaluated by measuring $IC_{50}$ values. Standard errors are determined by fitting of sigmoidal dose response curves using a four parameter logistic equation (De Lean, A., Munson, P. J., Guardabasso, V. and Rodbard, D. (1988) ALLFIT, Version 2.7, National Institute of Child Health and Human Development, N.I.H. Bethesda, Md., 1 diskette).

In the soleus muscle assay under the conditions described, preferred peptides of the invention act as amylin antagonists and have $IC_{50}$ values on the order of less than about 1 to 10 micromolar (µM). see Example 8. Positive results showing amylin antagonist activity in this in vitro assay have routinely been predictive of amylin antagonist activity in vivo. See, e.g., Example 10.

3. Selectivity Receptor Binding Assays

Other receptor binding assays can be used to demonstrate the selectivity of amylin antagonists for the amylin receptor.

As more fully described in Example 9, these assays, like the amylin receptor binding assay, are competition assays which measure the ability of compounds to bind specifically to certain membrane-bound receptors. Preferred sources of membrane preparations used in these assays are human SK-N-MC neuroblastoma cells and human T47D carcinoma cells to measure binding to CGRP and calcitonin receptors, respectively. Compounds being assayed compete for binding to the CGRP receptor preparations with $^{125}$I human αCGRP and to the calcitonin receptor preparations with $^{125}$I salmon calcitonin. Competition curves are analyzed as described for amylin receptor binding assays. The affinity of a compound for the amylin receptor relative to the affinity of the compound for the CGRP and calcitonin receptors determines the selectivity of the compound.

Peptides of the invention are selective for amylin receptors relative to CGRP and calcitonin receptors as may be determined by amylin, CGRP and calcitonin receptor binding assays. In the amylin, CGRP and calcitonin receptor binding assays, preferred peptides of the invention exhibit on the order of 10- to 50-fold greater selectivity for amylin receptors than CGRP and calcitonin receptors.

4. Infusion Studies

As shown in Example 10, infusion studies can be used to confirm or evaluate the activity of amylin antagonists in vivo.

Briefly, these studies are performed on anesthetized rats as described in International Application Number PCT/US92/00185, "Amylin Activity Assays", published Jul. 22, 1992. At time −0.5 hours, test rats are infused with a 1.5 mg bolus of the antagonist being tested followed by antagonist infusion at 3 mg/hr for a further 1.5 hours. At time 0 hours, a 50 µg bolus of amylin is administered followed by amylin infusion at 50 µg/hr for the remainder of the experiment. In these tests, the capacity of the antagonist to block the hyperglycemic and hyperlactemic effects of amylin are indicated by the inhibition of amylin-evoked increases in plasma glucose and plasma lactate. The ability of the antagonist to suppress the hypocalcemic and hypotensive actions of amylin are demonstrated in these tests by the amelioration of amylin-induced decreases in plasma calcium and blood pressure.

Peptides of the invention, when infused into rats, antagonize the hyperglycemia and hyperlactemia caused by the administration of amylin, and will be useful in the treatment of conditions associated with excess or undesired amylin activity, including Type 2 diabetes, obesity, insulin resistance, impaired glucose tolerance, and other disorders where amylin activity is beneficially reduced. For example, infusions of AAP30 (SEQ ID NO:30), AAP37 (SEQ ID NO:37) and AAP40 (SEQ ID NO:40) into rats was observed to prevent the hyperglycemic and hyperlactemic responses to amylin. See Example 10. The potency at which these peptides reversed the actions of amylin was found to be greater than expected, given the affinity of the peptides for amylin receptors as measured by the amylin receptor binding assay. As shown in Example 10, the peptides did not antagonize the hypotensive and/or hypocalcemic effects of amylin, indicating amylin receptor selectivity. As shown in Example 11, the amylin antagonist AAP40 (SEQ ID NO:40) effectively inhibits amylin-induced plasma renin activity in vivo and will be useful in the treatment of conditions associated with excess or undesired renin activity, such as hypertension.

SYNTHESIS OF PEPTIDES

The peptides of the invention may be prepared using standard solid-phase peptide synthesis techniques and preferably an automated or semiautomated peptide synthesizer. Typically, an α-N-carbamoyl protected amino acid and an amino acid attached to the growing peptide chain on a resin are coupled at room temperature in an inert solvent such as dimethylformamide, N-methylpyrrolidinone or methylene chloride in the presence of coupling agents such as dicyclohexylcarbodiimide and 1-hydroxybenzotriazole in the presence of a base such as diisopropylethylamine. The α-N-carbamoyl protecting group is removed from the resulting peptide-resin using a reagent such as trifluoroacetic acid or piperidine, and the coupling reaction repeated with the next desired N-protected amino acid to be added to the peptide chain. Suitable N-protecting groups are well known in the art, such as t-butyloxycarbonyl (tBoc), with fluorenylmethoxycarbonyl (Fmoc) being preferred herein.

The solvents and amino acid derivatives used in the peptide synthesizer were purchased from Applied Biosystems, Inc. (Foster City, Calif.), and the 4-(2'4'-dimethoxyphenyl)-Fmoc aminomethyl phenoxy resin was purchased from Novabiochem (La Jolla, Calif.), unless otherwise indicated. The side-chain protected amino acids used and purchased from Applied Biosystem Inc. included the following: Fmoc-Arg(Pmc), Fmoc-Thr(t-Bu), Fmoc-Ser (t-Bu), Fmoc-Tyr(t-Bu), Fmoc-Lys(Boc), Fmoc-Glu(t-Bu), Fmoc-His(Trt), Fmoc-Asn(Trt), and Fmoc-Gln(Trt).

Anisole, methylsulfide, phenol, ethanedithiol, and thioanisole were obtained from Aldrich Chemical Company (Milwaukee, Wis.). Ethyl ether, acetic acid and methanol were purchased from Fisher Scientific (Pittsburgh, Pa.).

Solid phase peptide synthesis was carried out with an automatic peptide synthesizer (Model 430A, Applied Biosystems, Inc., Foster City, Calif.) using the Fast Moc (HBTU) system and Fmoc chemistry (see Applied Biosystems Bulletin #31 for the ABI 431 Peptide Synthesizer, November 1990, pp. 1–26, Applied Biosystems, Inc., Foster City, Calif.). The Fmoc-peptide resins were cleaved according to standard methods (*Introduction to Cleavage Techniques*, Applied Biosystems, Inc., 1990, pp. 6–12). Some peptides were also assembled using an Advanced Chem Tech Synthesizer (Model MPS 350, Louisville, Ky.). Peptides were purified by RP-HPLC (preparative and analytical) using a Waters Delta Prep 3000 system. A C18 preparative column (10μ, 2.2×25 cm; Vydac, Hesperia, Calif.) was used to isolate peptides, and purity was determined using a C18 analytical column (5μ, 0.46×25 cm; Vydac). Solvents (A=0.1% TFA/water and B=0.1% TFA/$CH_3CN$) were delivered to the analytical column at a flowrate of 1.0 ml/min and to the preparative column at 15 ml/min. Amino acid analyses were performed on the Waters Pico Tag system and processed using the Maxima program. The peptides were hydrolyzed by vapor-phase acid hydrolysis (115° C., 20–24 h). Hydrolysates were derivatized and analyzed by standard methods (Cohen, S. A., Meys, M., and Tarrin, T. L. (1989), *The Pico Tag Method: A Manual of Advanced Techniques for Amino Acid Analysis*, pp. 11–52, Millipore Corporation, Milford, Mass.). Fast atom bombardment analysis was carried out by M-Scan, Incorporated (West Chester, Pa.). Mass calibration was performed using cesium iodide or cesium iodide/glycerol. Plasma desorption ionization analysis using time of flight detection was carried out on an Applied Biosystems Bio-Ion 20 mass spectrometer.

The peptides of the invention may also be prepared using recombinant DNA techniques, using methods now known in the art. See, e.g., Sambrook et al., *Molecular Cloning: A Laboratory Manual*, 2d Ed., Cold Spring Harbor (1989).

PREPARATION OF PEPTIDES AND PHARMACEUTICAL COMPOSITIONS

Peptides of the invention form salts with various inorganic and organic acids and bases. Such salts include salts prepared with organic and inorganic acids, for example, HCl, HBr, $H_2SO_4$, $H_3PO_4$, trifluoroacetic acid, acetic acid, formic acid, citric acid, methanesulfonic acid, toluenesulfonic acid, maleic acid, fumaric acid and camphorsulfonic acid. Salts prepared with bases include ammonium salts, alkali metal salts (e.g., sodium and potassium salts), and alkali earth salts (e.g., calcium and magnesium salts). Acetate, hydrochloride, and trifluoroacetate salts are preferred.

The salts may be formed by conventional means, as by reacting the free acid or base forms of the product with one or more equivalents of the appropriate base or acid in a solvent or medium in which the salt is insoluble, or in a solvent such as water which is then removed in vacuo or by freeze-drying or by exchanging the ions of an existing salt for another ion on a suitable ion exchange resin.

The peptides of the invention are useful in view of their pharmacological properties. In particular, peptides of the invention possess activity as anti-amylin agents, anti-diabetic agents as evidenced by their ability to reduce hyperglycemia in mammals, and anti-hypertensive agents as demonstrated by their ability to suppress renin activity in mammals. They will also be useful in the treatment of insulin resistance, impaired glucose tolerance and obesity. See, e.g., International Application Number PCT/US89/00049, "Treatment of Type 2 Diabetes Mellitus", PCT Publication Number WO 89/06135, published Jul. 13, 1989, and International Application Number 90307502.6, "Treatment of Obesity and Essential Hypertension and Related Disorders," Publication Number EP 0 408 294 A2, published Jan. 16, 1991, which describe the use of amylin antagonists for treatment of Type 2 diabetes, insulin resistance, obesity, and essential hypertension.

Products of the invention may conveniently be provided in the form of compositions or solutions suitable for parenteral (including intravenous, intramuscular and subcutaneous), nasal, transdermal, oral or direct (e.g., through a medical pump) administration. In some cases, it will be convenient to provide an amylin antagonist of the invention and another agent, such as another hypoglycemic agent (e.g. a sulfonylurea) in a single composition or solution for administration together, or it will be convenient to provide an amylin antagonist of the invention and another anti-hypertensive agent, such as an ACE inhibitor, in a single composition or solution. In other cases, it may be more advantageous to administer a sulfonylurea or other hypoglycemic agent separately from said amylin antagonist, or it may be more advantageous to administer an ACE inhibitor or other anti-hypertensive agent (such as a diuretic, a cardiotonic agent, or a beta-adrenergic blocker) separately from the amylin antagonist. A suitable administration format may best be determined by a medical practitioner for each patient individually. Suitable pharmaceutically acceptable carriers and their formulations are described in standard formulation treatises, e.g., *Remington's Pharmaceutical Sciences* by E. W. Martin. See also Wang, Y. J. and Hanson, M. A. "Parenteral Formulations of Proteins and Peptides: Stability and Stabilizers," *Journal of Parenteral Science and Technology*, Technical Report No. 10, Supp. 42:2S (1988). Suitable formulations including hypoglycemic agents such as sulfonylureas and anti-hypertensive agents such as ACE inhibitors are known in the art.

The products of the invention will normally be provided as parenteral compositions for injection or infusion. They can, for example, be suspended in an inert oil, suitably a vegetable oil such as sesame, peanut, olive oil, or other acceptable carrier. Preferably, they are freeze-dried or suspended in an aqueous carrier, for example, in an isotonic buffer solution at a pH of about 4.0 to 7.4. These compositions may be sterilized by conventional sterilization techniques, or may be sterile filtered. The compositions may contain pharmaceutically acceptable auxiliary substances as required to approximate physiological conditions, such as pH buffering agents. Useful buffers include sodium citrate-citric acid, sodium acetate-acetic acid and sodium phosphate-phosphoric acid. A form of repository or "depot" slow release preparation may be used so that therapeutically effective amounts of the preparation are delivered into the bloodstream over many hours or days following transdermal injection or delivery.

The desired isotonicity may be accomplished using sodium chloride or other pharmaceutically acceptable agents such as dextrose, boric acid, sodium tartrate, propylene glycol, polyols (such as mannitol and sorbitol), or other inorganic or organic solutes. Sodium chloride is preferred particularly for buffers containing sodium ions.

If desired, solutions of the above compositions may be thickened with a thickening agent such as methyl cellulose.

They may be prepared in emulsified form, either water in oil or oil in water. Any of a wide variety of pharmaceutically acceptable emulsifying agents may be employed including, for example, acacia powder, a non-ionic surfactant (such as a Tween), or an ionic surfactant (such as alkali polyether alcohol sulfates or sulfonates).

The therapeutically useful compositions of the invention are prepared by mixing the ingredients following generally accepted procedures. For example, the selected components may be simply mixed in a blender or other standard device to produce a concentrated mixture which may then be adjusted to the final concentration and viscosity by the addition of water or thickening agent and possibly a buffer to control pH or an additional solute to control tonicity.

For use by the physician, the compositions will be provided in dosage unit form containing an amount of an antagonist peptide of the invention with or without another agent which will be effective in one or multiple doses to control or reestablish blood sugar at the selected level, or an amount of an antagonist peptide of the invention with or without another anti-hypertensive agent with will be effective in one or multiple doses to control or reestablish blood pressure at a selected level. Therapeutically effective amounts of an amylin antagonist as described herein for the treatment of Type 2 diabetes mellitus and impaired glucose tolerance are those that decrease blood sugar levels, preferably to below from about 140 to about 190 mg/dl (fasted and fed, respectively). Therapeutically effective amounts of an amylin antagonist for the treatment of insulin resistance are those that increase the effectiveness of insulin, preferably by at least about 20%, as may be determined using methods described herein and known in the art. Therapeutically effective amounts of an amylin antagonist for the treatment of obesity are those that reduce amylin activity by at least about 25% or that increase the weight loss associated with diet. Therapeutically effective amounts of an amylin antagonist for the treatment of hypertension and other such conditions in which renin activity is beneficially reduced are those that decrease blood renin activity, preferably to no more than about 50% of pretreatment levels, or such that blood pressure levels are reduced as desired. In some hypertensive individuals, plasma renin activity is not higher than in normotensive individuals, and in such hypertensive individuals, beneficial reduction of arterial pressure, for example, may be obtained without changes in plasma renin activity (see Wilson, J. D. and Foster, D. W., *Williams Text Book of Endocrinology*, page 714 (8th Edition 1992)). As will be recognized by those in the field, an effective amount of therapeutic agent will vary with many factors including the sex, age and weight of the patient, the patient's physical or medical condition, the blood sugar level or decrease in amylin activity to be obtained, and other factors.

Such pharmaceutical compositions are useful in the treatment of Type 2 diabetes mellitus and hypertension, as well as other disorders where amylin activity is beneficially reduced, as described.

The effective daily antidiabetic and antihypertensive dose of the compounds of this invention will typically be in the range of 0.05 to about 1000 mg/day, preferably about 1 to 500 mg/day for a 70 kg patient, administered in a single or divided doses. The exact dose to be administered is determined by the attending clinician and is dependent upon where the particular compound lies within the above quoted range, as well as upon the age, weight and condition of the individual. Administration should begin at the first sign of symptoms or shortly after diagnosis of diabetes mellitus and hypertension.

Generally, in treating humans having Type 2 diabetes mellitus and hypertension, the compounds of the invention may be administered to patients in need of such treatment in a dosage range of about 0.1 mg to 50 mg per patient generally given several times a day, thus giving a total dose of from about 0.3 mg to 200 mg per day.

To assist in understanding the invention, the following Examples are included which describe the results of a series of experiments. The following examples relating to the invention should not, of course, be construed in specifically limiting the invention and such variations of the invention, now known or later developed, which would be within the purview of one skilled in the art are considered to fall within the scope of the invention as described herein and hereinafter claimed.

EXAMPLES

Example 1

Preparation of AAP40 (SEQ ID NO:40)

The peptide was assembled on 4-(2',4'-dimethoxyphenyl)-Fmoc aminomethyl phenoxy resin (Novabiochem, 0.44 mole/g) using Fmoc-protected amino acids from Applied Biosystems, Inc. Single-coupling cycles were used throughout the synthesis and Fast Moc (HBTU activation) chemistry. Acetylation was accomplished by the ENDCAP program using acetic anhydride. The completed peptide resin was deprotected and cleaved using a mixture of phenol (0.75 g), ethanedithiol (0.25 ml), thioanisole (0.5 ml), water (0.5 ml) and trifluoroacetic acid (10 ml) according to standard methods (*Introduction to Cleavage Techniques*, Applied Biosystems, Inc., 1990, pp. 6–12). The lyophilized crude product was applied to a preparative C18 column and gradient purified (100% A/0% B to 60% A/40% B over 45 minutes). Purity of fractions was determined isocratically using a C18 analytical column (75% A/25% B to 50% A/50% B over 30 minutes. Pure fractions were pooled furnishing white peptide (99% pure fractions, 98 mg). Analytical RP-HPLC (75% A/25% B to 50% A/50% B over 30 minutes) of the lyophilized peptide pool indicated a purity of 99%. Amino acid analysis (6M HCl, 115°) showed the following: Ala, 1.98 (2); Arg, 3.05 (3); Asx, 3.02 (3); Glx, 3.08 (3); Gly, 1.05 (1); Leu, 3.15 (3); Pro 1.00 (1); Ser, 0.99 (1); Thr, 3.87 (4); Tyr, 1.85 (2); Val, 1.91 (2). FAB Mass Spectrometry: $(M+H)^+$ Calculated: 2908.3; Found: 2908.4.

Example 2

Preparation of AAP29 (SEQ ID NO:29)

The peptide was prepared in a manner similar to that described in Example 1. FAB Mass Spectrometry: $(M+H)^+$ Calculated: 2879.2; Found: 2879.2.

Example 3

Preparation of AAP30 (SEQ ID NO:30)

The peptide was prepared in a manner similar to that described in Example 1. FAB Mass Spectrometry: $(M+H)^+$ Calculated: 2864.2; Found: 2864.2.

Example 4

Preparation of AAP37 (SEQ ID NO:37)

The peptide was prepared in a manner similar to that described in Example 1. FAB Mass Spectrometry: $(M+H)^+$ Calculated: 2907.3; Found: 2907.3.

Example 5

Preparation of AAP38 (SEQ ID NO:38)

The peptide was prepared in a manner similar to that described in Example 1. FAB Mass Spectrometry: (M+H)$^+$ Calculated: 2865.2; Found: 2865.2.

Example 6

Preparation of AAP39 (SEQ ID NO:39)

The peptide was prepared in a manner similar to that described in Example 1. FAB Mass Spectrometry: (M+H)$^+$ Calculated: 2880.2; Found: 2880.2.

Example 7

Amylin Receptor Binding Assays With AAP29 (SEQ ID NO:29), AAP30 (SEQ ID NO:30), AAP37 (SEQ ID NO:37), AAP38 (SEQ ID NO:38), AAP39 (SEQ ID NO:39), and AAP40 (SEQ ID NO:40)

To determine the affinity of the peptides for amylin receptors, an in vitro radioligand binding assay was used. Nucleus accumbens and surrounding regions, the membranes of which have been demonstrated to contain a high density of amylin receptors, were dissected from male Sprague-Dawley rat brains. Tissue was homogenized in ice-cold 20 mM HEPES buffer, pH 7.4, and membranes were sedimented by centrifuging for 15 min at 48,000×g. Membranes were resuspended in fresh buffer and centrifuged twice more, then the final membrane pellet was resuspended in 20 mM HEPES buffer containing 0.2 mM phenylmethylsulfonyl fluoride (PMSF). Membranes from 4 mg original wet weight of tissue were incubated with $^{125}$I rat amylin (Bolton-Hunter labeled at the N-terminal lysine, specific activity ranging from 1950 to 2000 Ci/mmol) at 14 pM in 20 mM HEPES buffer containing bacitracin, bovine serum albumin, and PMSF to reduce proteolysis. Solutions were incubated for 60 minutes at 23° C. and were terminated by filtration through polyethyleneimine-treated glass fiber filters. Filters were washed with 15 ml cold phosphate-buffered saline and radioactivity assessed in a gamma-counter. Total binding varied from 2400–3000 cpm/0.2 ml, with nonspecific binding measured in the presence of $10^{-7}$M human amylin accounting for 40–45% of total binding. Competition curves were generated by measuring binding of the $^{125}$I rat amylin in the presence of $10^{-13}$ to $10^{-7}$M unlabeled peptide and were fit to a 4-parameter logistic equation by a nonlinear regression program. The IC$_{50}$ of AAP29 (SEQ ID NO:29) for $^{125}$I rat amylin binding to rat brain membranes was 1.1 nM, that of AAP30 (SEQ ID NO:30) was 1.6 nM, that of AAP37 (SEQ ID NO:37) was 0.21 nM, that of AAP38 (SEQ ID NO:38) was 3.5 nM, that of AAP39 (SEQ ID NO:39) was 3.6 nM, and that of AAP40 (SEQ ID NO:40) was 0.50 nM.

Example 8

Soleus Muscle Assays With AAP30 (SEQ ID NO:30), AAP37 (SEQ ID NO:37) and AAP40 (SEQ ID NO:40)

These assays involving the stimulation by insulin of glycogen synthesis in rat soleus muscle in vitro were performed as described by Young, A. A. et al., *Am. J. Physiol.* 263:E274–281 (1992). Rat amylin inhibited the insulin-stimulated incorporation of radiolabelled glucose into glycogen.

The effects of the peptide in the rat soleus muscle glycogenesis system were measured according to the following method. Insulin-stimulated radioglucose incorporation was measured as described above in the presence of 100 nM rat amylin to maximally suppress incorporation. Increasing concentrations of AAP30 (SEQ ID NO:30), AAP37 (SEQ ID NO:37) and AAP40 (SEQ ID NO:40) were added to test their antagonism of amylin, i.e., to increase radioglucose incorporation under these conditions. The results demonstrated that the peptides antagonized the effects of 100 nM amylin on insulin-stimulation of glycogenesis in skeletal muscle with IC$_{50}$'s of 1.13 µM, 4.59 µM and 135.88 nM, respectively.

Example 9

Selectivity Receptor Binding Assays With AAP30 (SEQ ID NO:30), AAP37 (SEQ ID NO:37) and AAP40 (SEQ ID NO:40)

The selectivity of antagonist peptides for the amylin receptor relative to the CGRP and calcitonin receptors was determined by using two in vitro radioligand binding assays and comparing the results obtained to those acquired from the amylin receptor binding assay described in Example 7.

To measure the affinity of the peptides for CGRP receptors, human SK-N-MC neuroblastoma cells were used. The membranes of these cells have been shown to contain a high affinity CGRP receptor which has binding and specificity characteristics similar to CGRP receptors present in several other tissues. Van Valen, Piechot & Jurgens, *Neuroscience Letters* 119:195–198 (1990). SK-N-MC cells were homogenized in 50 mM HEPES buffer, pH 7.4, and membranes were collected by centrifugation for 15 min at 48,000×g. Membranes were suspended at 0.1 to 0.2 mg protein/0.2 ml assay and were incubated in 50 mM HEPES, pH 7.4 containing BSA, bacitracin, and 2 mM MgCl$_2$ with 20 pM $^{125}$I human αCGRP (labeled at $^{10}$his, 2000 Ci/mmol) and unlabeled peptide. Additional methods were similar to those described for amylin receptor binding assays in Example 2. The IC$_{50}$ of AAP40 (SEQ ID NO:40) for $^{125}$I human αCGRP binding to human SK-N-MC cell membranes was 33 nM. The IC$_{50}$ of the peptide for $^{125}$I rat amylin binding to rat brain membranes was 0.50 nM (see Example 2), and AAP40 (SEQ ID NO:40) was therefore shown to be 66-fold more selective for amylin receptors than CGRP receptors. The IC$_{50}$ of AAP37 (SEQ ID NO:37) in the CGRP receptor binding assay was 2.6 nM; comparison with its IC$_{50}$ value in the amylin receptor binding assay of 0.21 nM shows that AAP37 (SEQ ID NO:37) is 12-fold more selective for amylin receptors than CGRP receptors. The IC$_{50}$ of AAP30 (SEQ ID NO:30) in the CGRP receptor binding assay was 69 nM; comparison with its IC$_{50}$ value in the amylin receptor binding assay of 1.6 nM shows that AAP30 (SEQ ID NO:30) is 43-fold more selective for amylin receptors than CGRP receptors.

To determine the affinity of the antagonist peptides for calcitonin receptors, human T47D carcinoma cells were used. The membranes of these cells have been shown to contain high densities of calcitonin receptors similar to those present in bone. Findlay et al., *Cancer Research* 40:4764–4767 (1980). Membranes were prepared from confluent cultures of T47D cells as described for SK-N-MC cells. Membranes were incubated with $^{125}$I salmon calcitonin (labeled at $^{22}$tyr, 2000 Ci/mmol) at a concentration of 30 pM for 60 minutes at ambient temperature. Additional methods were similar to those described for amylin receptor binding assays in Example 2. The IC$_{50}$ of AAP40 (SEQ ID NO:40) for $^{125}$I salmon calcitonin binding to human T47D cell membranes was 50 nM. Based on the $IC_{50}$ of the peptide for $^{125}$I rat amylin binding to rat brain membranes, which was 0.50 nM (see Example 2), it is concluded that AAP40 (SEQ ID NO:40) is 100-fold more selective for amylin receptors than calcitonin receptors. The $IC_{50}$ of AAP37 (SEQ ID NO:37) in the calcitonin receptor binding assay was 160 nM; comparison with its $IC_{50}$ value in the amylin receptor binding assay of 0.21 nM shows that AAP37 (SEQ ID NO:37) is 762-fold more selective for amylin receptors than CGRP receptors. The $IC_{50}$ of AAP30 (SEQ ID NO:30) in the CGRP receptor binding assay was 36 nM; comparison with its $IC_{50}$ value in the amylin receptor binding assay of 1.6 nM shows that AAP30 (SEQ ID NO:30) is 22-fold more selective for amylin receptors than CGRP receptors.

Example 10

Infusion Studies With AAP30 (SEQ ID NO:30), AAP37 (SEQ ID NO:37) and AAP40 (SEQ ID NO:40)

Amylin antagonists were evaluated in vivo for their ability to inhibit amylin-induced elevation of plasma glucose and plasma lactate and amylin-evoked depression of plasma calcium and blood pressure. Male Harlan Sprague Dawley rats (age 75–85 days, mass 300–350 g) fasted 18–20 hours were halothane anesthetized and cannulated via the saphenous vein for infusions/injections and via the femoral artery for sampling of glucose/lactate/calcium and for recording arterial pressure. One and a half hours after surgery they were infused with a 1.5 mg intravenous bolus of test antagonist, followed by an infusion of 3 mg/hour for a further 1.5 hours (t=−0.5→+1.0 hr). At t=0 hours (0.5 hours after the start of the primed/continuous antagonist infusion) a 50 µg intravenous bolus of rat amylin was administered followed by an infusion of 50 µg/hour which continued until the end of the experiment. Blood samples were collected every 10 minutes for the first 2 hours of the test (then less frequently), and mean arterial pressure was continuously recorded from t=−0.5→t=+0.5 hours. Control rats, not administered the test substance, were injected with either saline or with primed/continuous amylin at t=0 hours, as described above.

FIGS. 1–4 illustrate the results of the evaluation of AAP40 (SEQ ID NO:40). Shown is the change in in vivo response when amylin is administered in the presence of AAP40 (SEQ ID NO:40), as well as the change in in vivo response in amylin control and saline control animals. The results depicted in FIGS. 1 and 2 indicate that intravenous infusion of AAP40 (SEQ ID NO:40) into anesthetized rats suppressed the increases in plasma glucose and plasma lactate normally evoked by rat amylin. Given the affinity of AAP40 (SEQ ID NO:40) for the amylin receptor as determined by the amylin receptor binding assay, the potency at which AAP40 (SEQ ID NO:40) blocked amylin-induced hyperglycemia and hyperlactemia was greater than expected.

Figure 3:
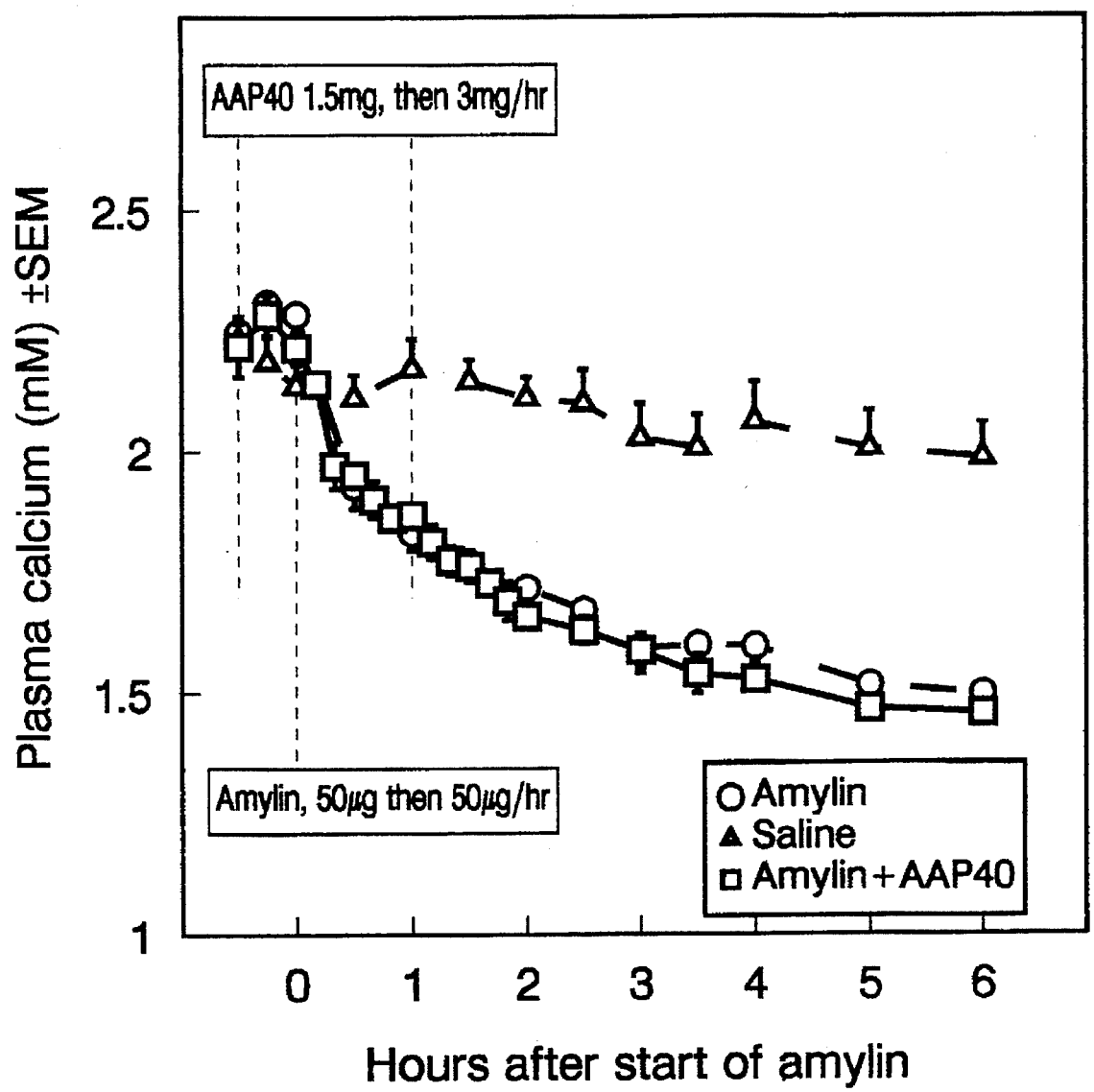
FIG. 3 illustrates the effect of prior infusion of AAP40 (SEQ ID NO:40) on amylin-induced hypocalcemia. Plasma calcium (mM)±SEM is plotted as a function of hours after start of amylin. Test animals were infused with a 1.5 mg bolus of AAP40 (SEQ ID NO:40), followed by an infusion of 3 mg/hr for a further 1.5 hours. At t=0 hours (0.5 hours after the start of the AAP40 (SEQ ID NO:40) infusion) a 50 µg bolus of amylin was administered followed by an infusion of 50 μg/hour which continued until the end of the experiment. Squares indicate the response when amylin is administered in the presence of AAP40 (SEQ ID NO:40), circles, when amylin is administered alone, and triangles, when saline is administered instead of amylin.
Figure 4:
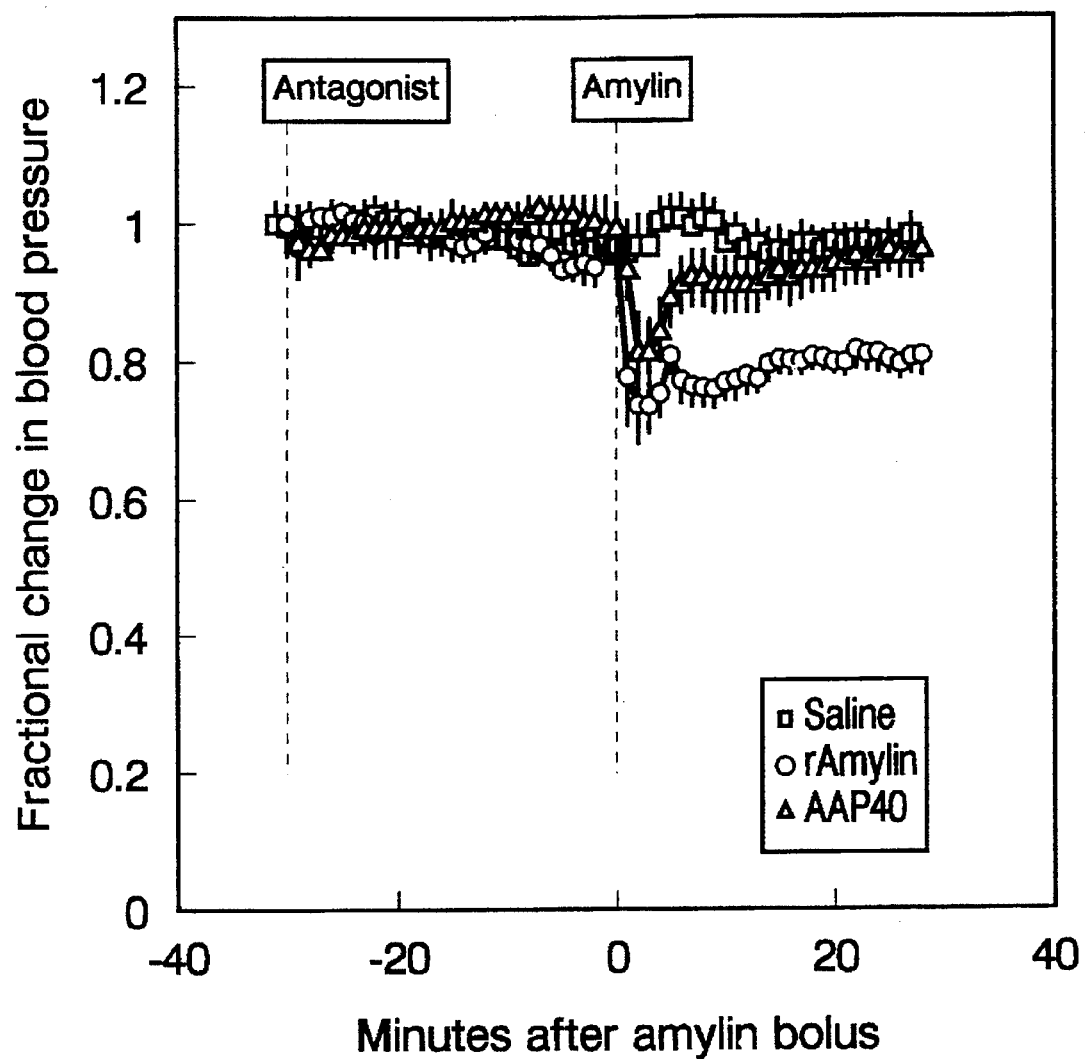
FIG. 4 illustrates the effect of prior infusion of AAP40 (SEQ ID NO:40) on amylin-induced hypotension. Fractional change in blood pressure (normalized so that blood pressure just before amylin administration=1.0)±SEM is plotted as a function of minutes after start of amylin. Test animals were infused with a 1.5 mg bolus of AAP40 (SEQ ID NO:40), followed by an infusion of 3 mg/hr for a further 1.5 hours. At t=0 hours (0.5 hours after the start of the AAP40 (SEQ ID NO:40) infusion) a 50 μg bolus of amylin was administered followed by an infusion of 50 μg/hour which continued until the end of the experiment. Triangles indicate the response when amylin is administered in the presence of AAP40 (SEQ ID NO:40), circles, when amylin is administered alone, and squares, when saline is administered instead of amylin.
Figure 5:
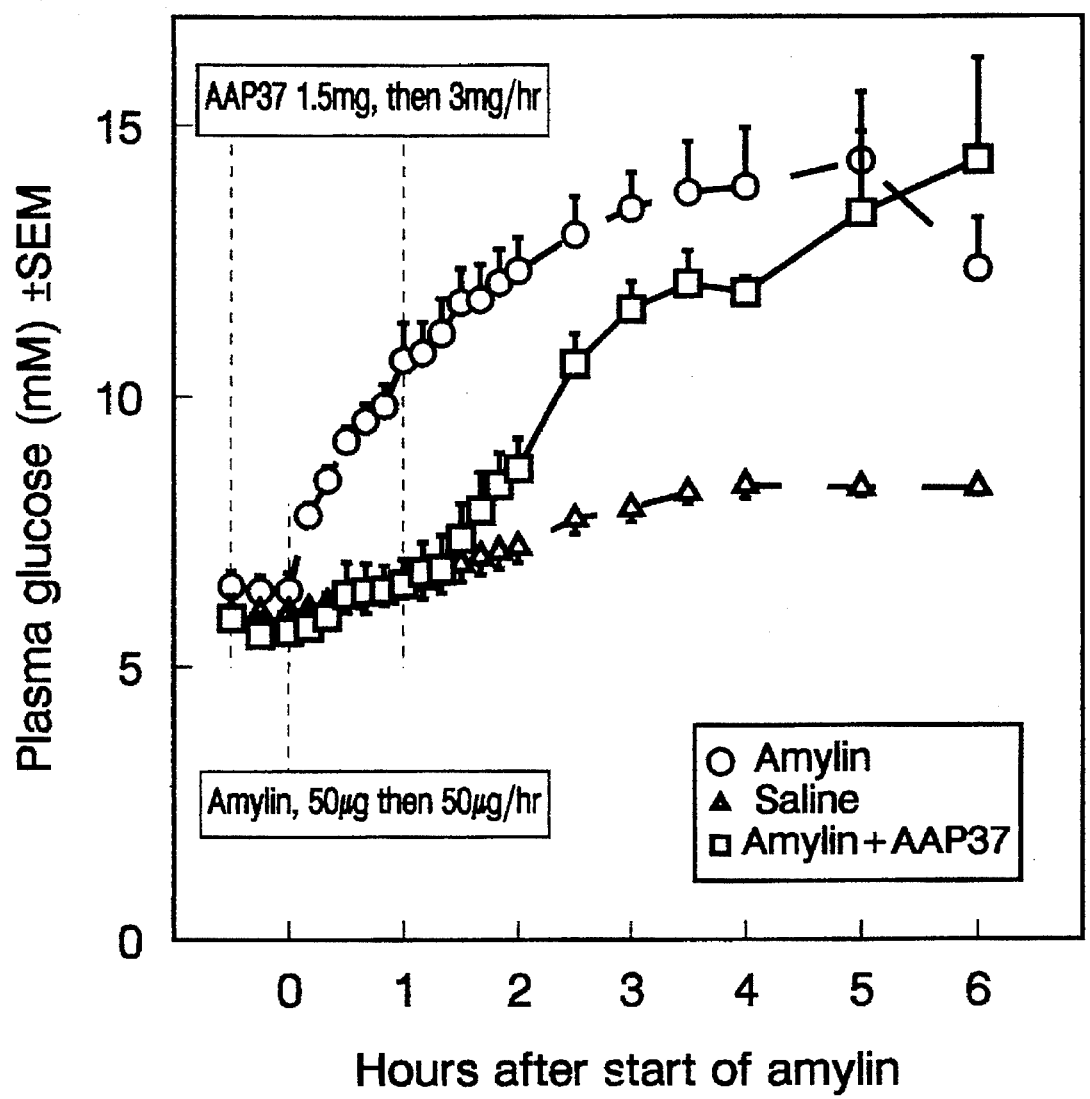
FIG. 5 illustrates the inhibition of amylin-induced hyperglycemia by prior infusion with AAP37 (SEQ ID NO:37). Plasma glucose (mM)±SEM is plotted as a function of hours after start Test animals were infused with a 1.5 mg bolus of AAP37 (SEQ ID NO:37), followed by an infusion of 3 mg/hr for a further 1.5 hours. At t=0 hours (0.5 hours after the start of the AAP37 (SEQ ID NO:37) infusion) a 50 μg bolus of amylin was administered followed by an infusion of 50 μg/hour which continued until the end of the experiment. Squares indicate the response when amylin is administered in the presence of AAP37 (SEQ ID NO:37), circles, when amylin is administered alone, and triangles, when saline is administered instead of amylin.
Figure 6:
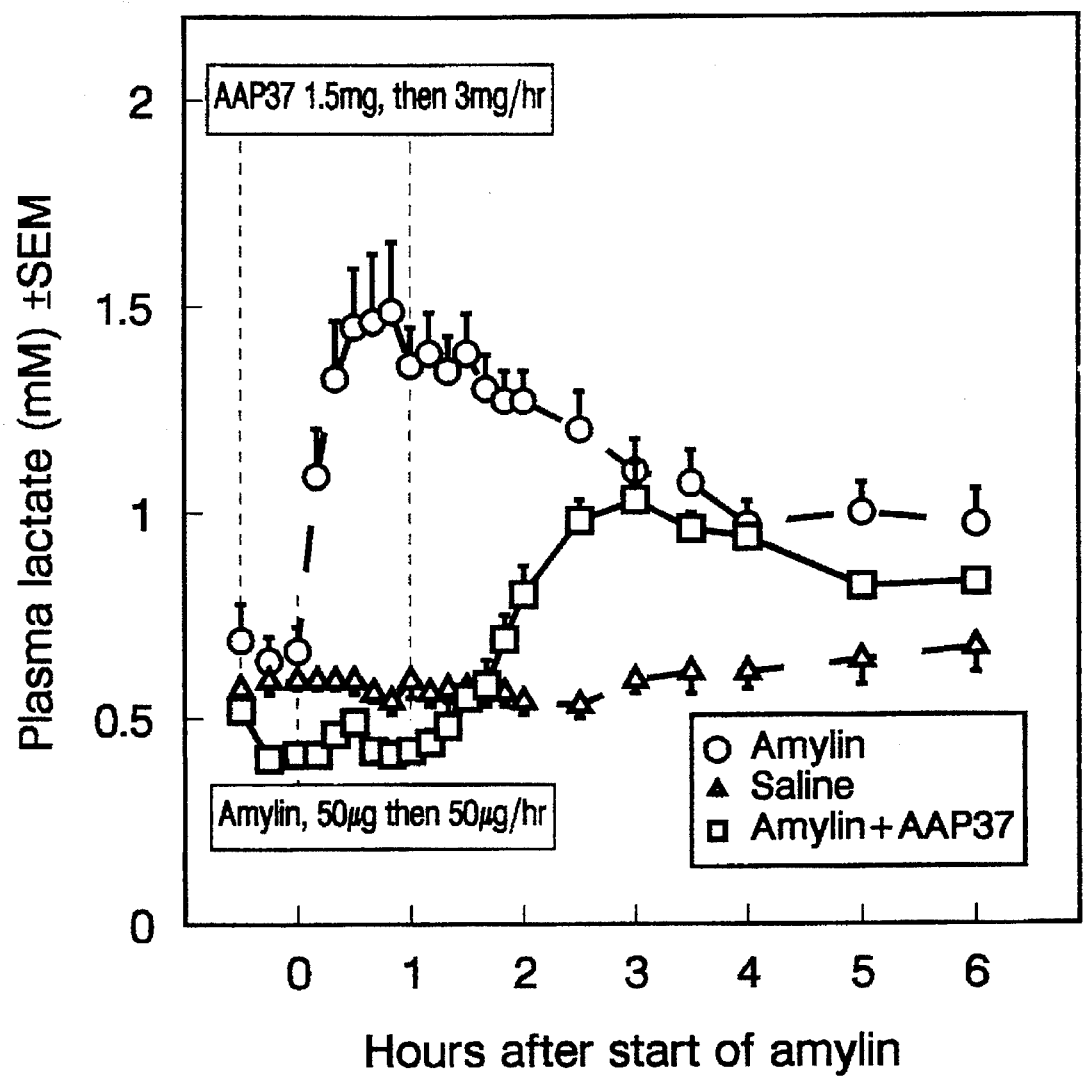
FIG. 6 illustrates the inhibition of amylin-induced hyperlactemia by prior infusion with AAP37 (SEQ ID NO:37). Plasma lactate (mM)±SEM is plotted as a function of hours after start of amylin. Test animals were infused with a 1.5 mg bolus of AAP37 (SEQ ID NO:37), followed by an infusion of 3 mg/hr for a further 1.5 hours. At t=0 hours (0.5 hours after the start of the AAP37 (SEQ ID NO:37) infusion) a 50 μg bolus of amylin was administered followed by an infusion of 50 μg/hour which continued until the end of the experiment. Squares indicate the response when amylin is administered in the presence of AAP37 (SEQ ID NO:37), circles, when amylin is administered alone, and triangles, when saline is administered instead of amylin.

The results illustrated in FIGS. 3 and 4 indicate that intravenous infusion of AAP40 (SEQ ID NO:40) into anesthetized rats did not inhibit the decreases in plasma calcium and blood pressure induced by rat amylin, i.e., that AAP40 (SEQ ID NO:40) is selective for receptors that mediate the hyperglycemic and hyperlactemic actions of amylin relative to those receptors that mediate the hypocalcemic and hypotensive effects of amylin.

Figure 7:
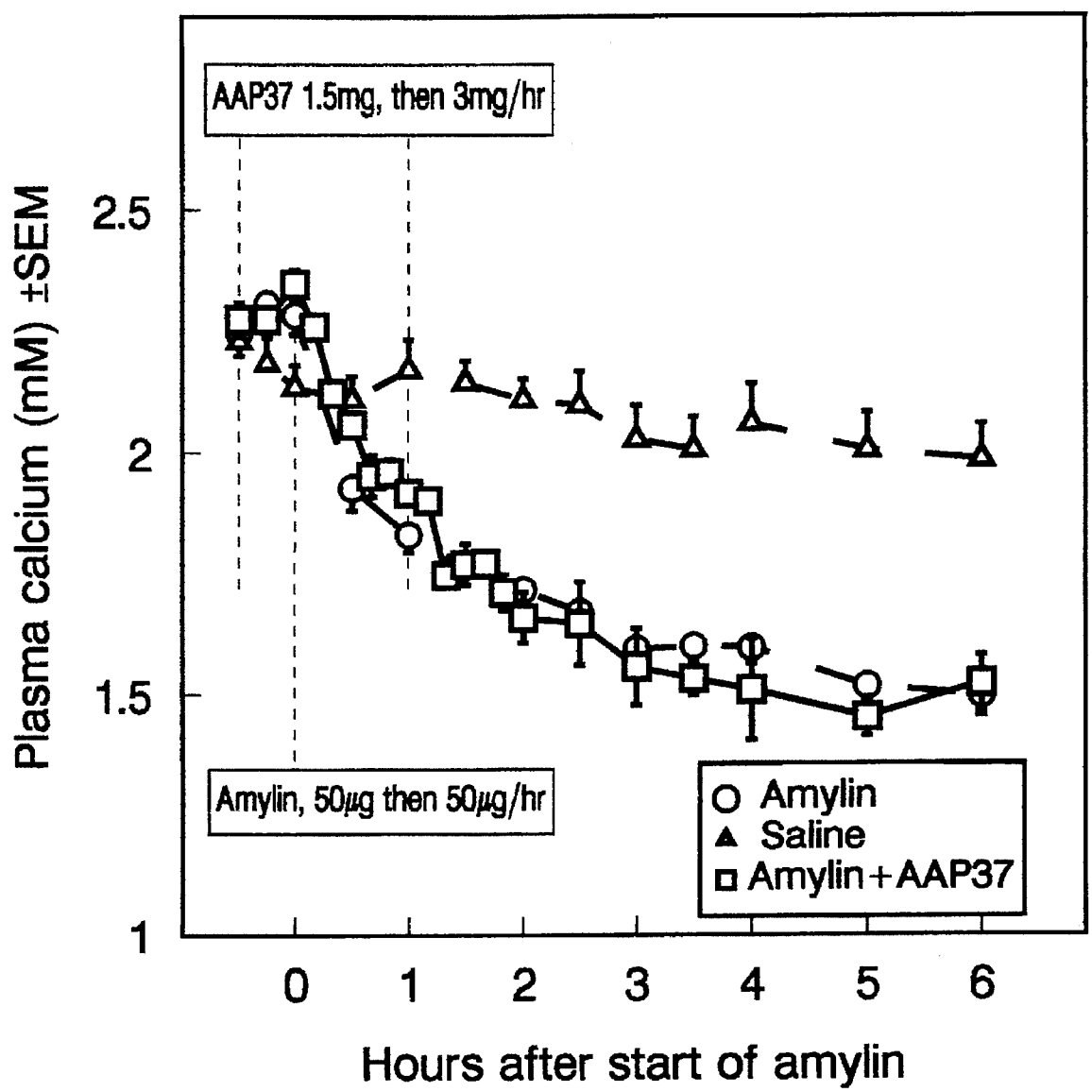
FIG. 7 illustrates the effect of prior infusion of AAP37 (SEQ ID NO:37) on amylin-induced hypocalcemia. Plasma calcium (mM)±SEM is plotted as a function of hours after start of amylin. Test animals were infused with a 1.5 mg bolus of AAP37 (SEQ ID NO:37), followed by an infusion of 3 mg/hr for a further 1.5 hours. At t=0 hours (0.5 hours after the start of the AAP37 (SEQ ID NO:37) infusion) a 50 μg bolus of amylin was administered followed by an infusion of 50 μg/hour which continued until the end of the experiment. Squares indicate the response when amylin is administered in the presence of AAP37 (SEQ ID NO:37), circles, when amylin is administered alone, and triangles, when saline is administered instead of amylin.
Figure 8:
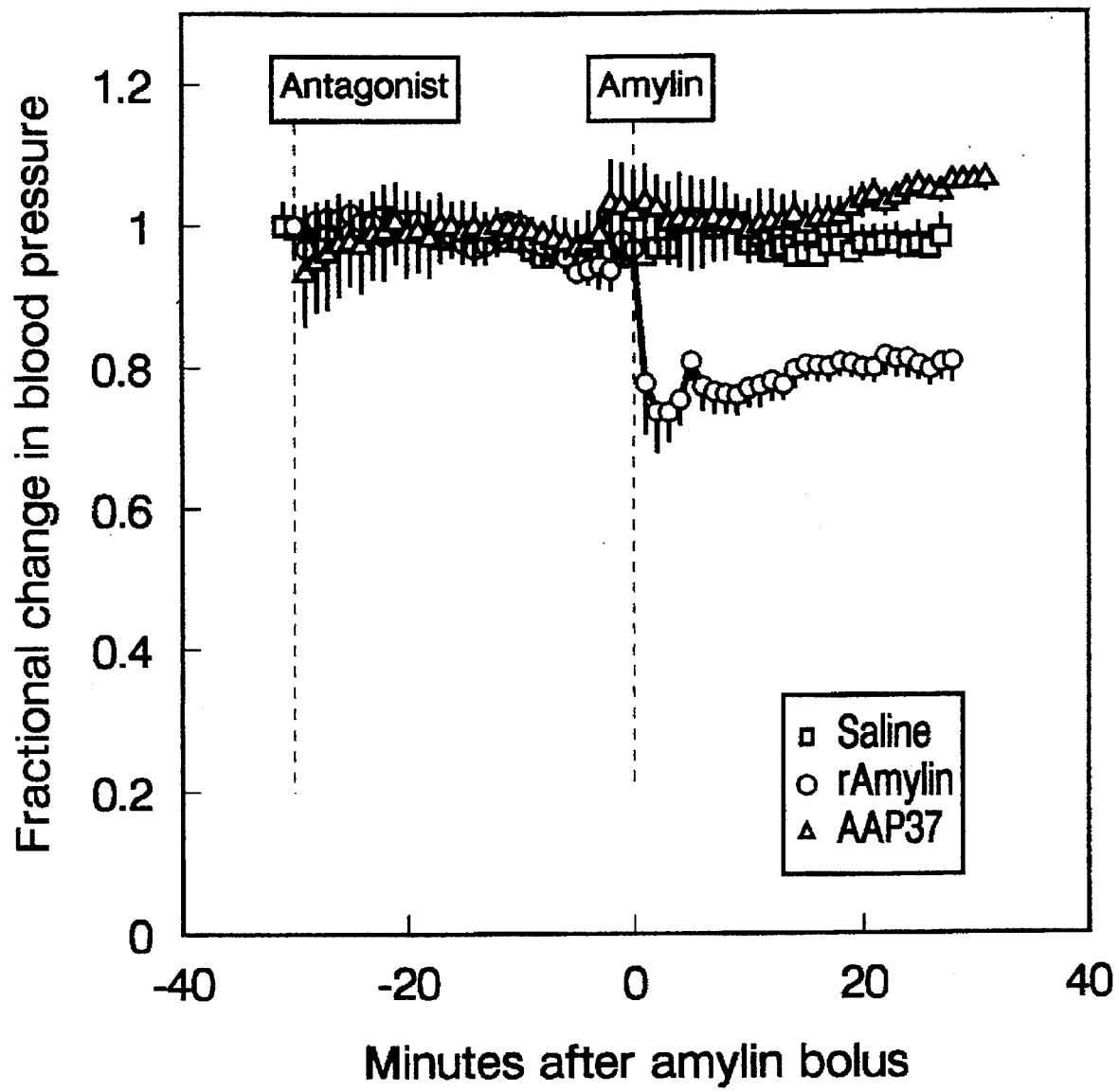
FIG. 8 illustrates the effect of prior infusion of AAP37 (SEQ ID NO:37) on amylin-induced hypotension. Fractional change in blood pressure (normalized so that blood pressure just before amylin administration=1.0)±SEM is plotted as a function of minutes after start of amylin. Test animals were infused with a 1.5 mg bolus of AAP37 (SEQ ID NO:37), followed by an infusion of 3 mg/hr for a further 1.5 hours. At t=0 hours (0.5 hours after the start of the AAP37 (SEQ ID NO:37) infusion) a 50 μg bolus of amylin was administered followed by an infusion of 50 μg/hour which continued until the end of the experiment. Triangles indicate the response when amylin is administered in the presence of AAP37 (SEQ ID NO:37), circles, when amylin is administered alone, and squares, when saline is administered instead of amylin.
Figure 9:
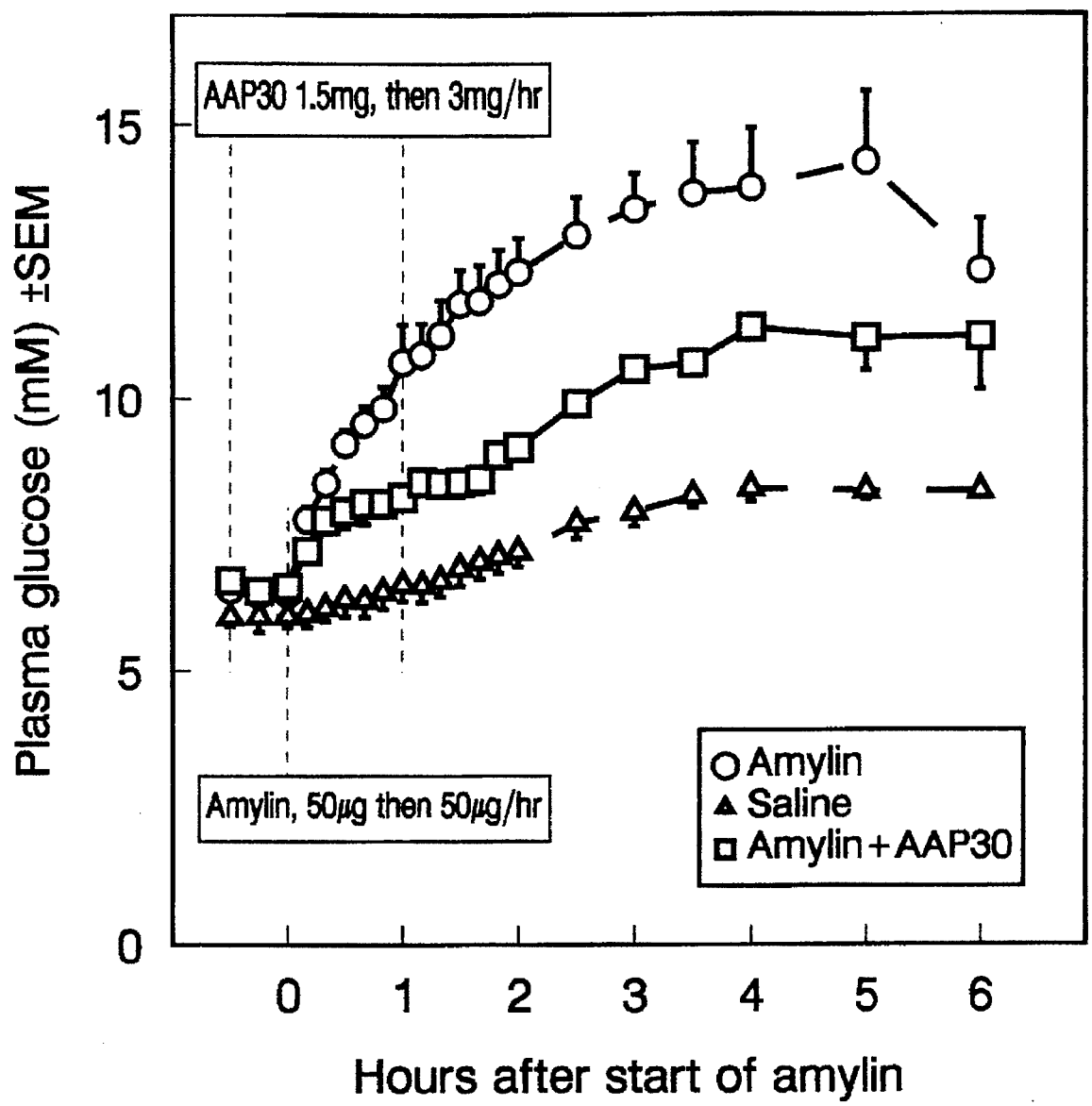
FIG. 9 illustrates the inhibition of amylin-induced hyperglycemia by prior infusion with AAP30 (SEQ ID NO:30). Plasma glucose (mM)±SEM is plotted as a function of hours after start of amylin. Test animals were infused with a 1.5 mg bolus of AAP30 (SEQ ID NO:30), followed by an infusion of 3 mg/hr for a further 1.5 hours. At t=0 hours (0.5 hours after the start of the AAP30 (SEQ ID NO:30) infusion) a 50 μg bolus of amylin was administered followed by an infusion of 50 μg/hour which continued until the end of the experiment. Squares indicate the response when amylin is administered in the presence of AAP30 (SEQ ID NO:30), circles, when amylin is administered alone, and triangles, when saline is administered instead of amylin.
Figure 10:
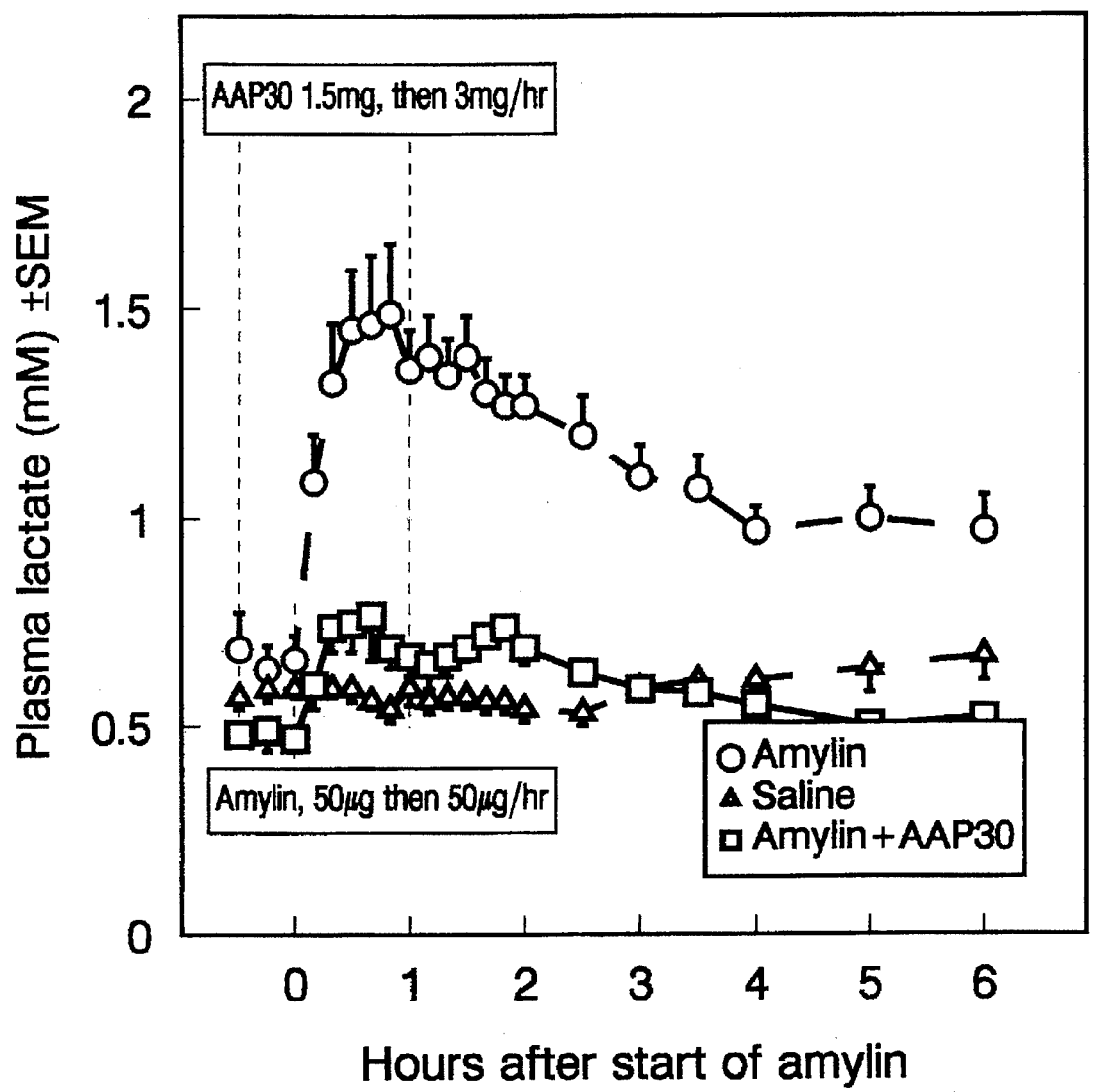
FIG. 10 illustrates the inhibition of amylin-induced hyperlactemia by prior infusion with AAP30 (SEQ ID NO:30). Plasma lactate (mM)±SEM is plotted as a function of hours after start of amylin. Test animals were infused with a 1.5 mg bolus of AAP30 (SEQ ID NO:30), followed by an infusion of 3 mg/hr for a further 1.5 hours. At t=0 hours (0.5 hours after the start of the AAP30 (SEQ ID NO:30) infusion) a 50 μg bolus of amylin was administered followed by an infusion of 50 μg/hour which continued until the end of the experiment. Squares indicate the response when amylin is administered in the presence of AAP30 (SEQ ID NO:30), circles, when amylin is administered alone, and triangles, when saline is administered instead of amylin.
Figure 11:
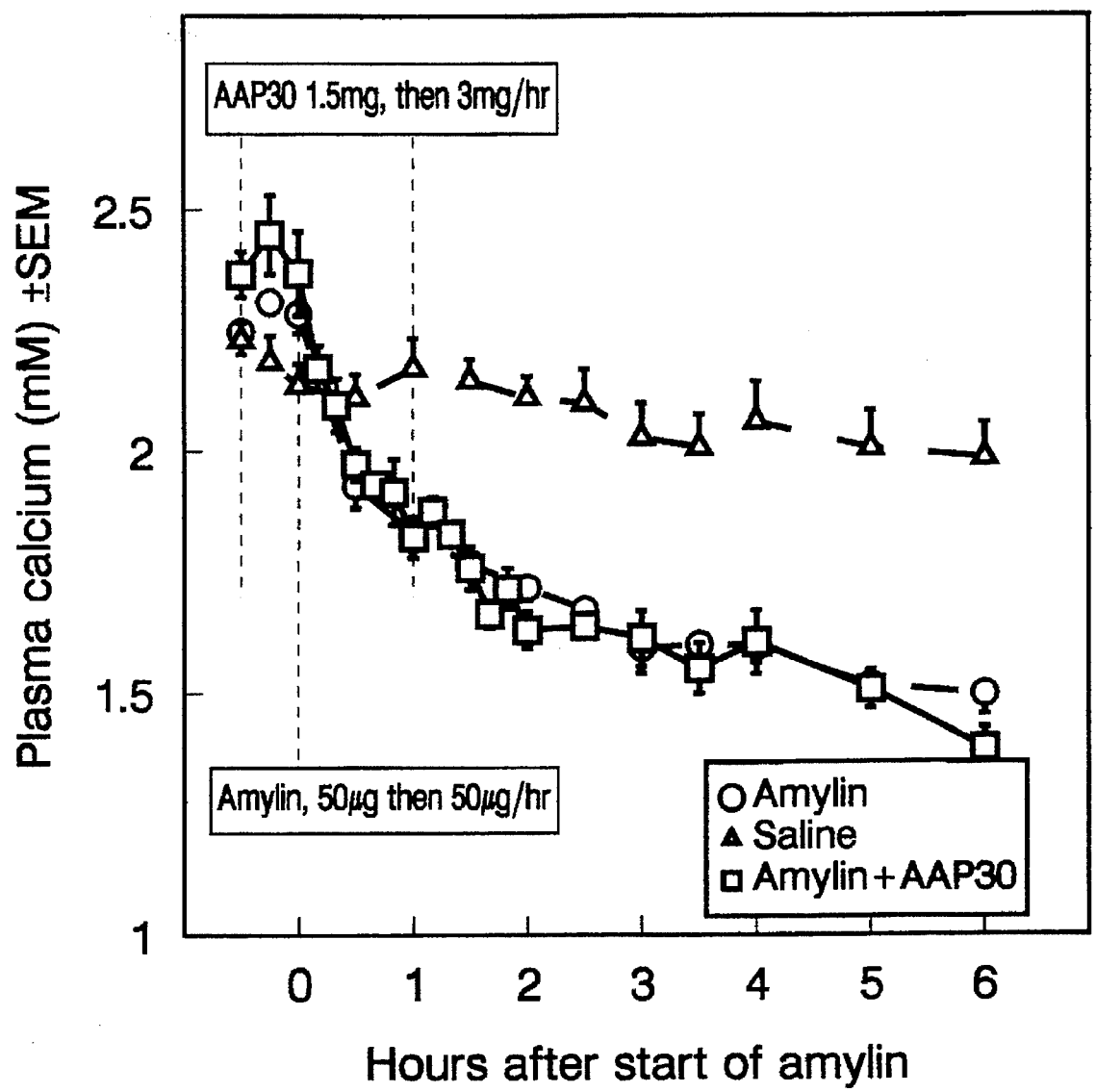
FIG. 11 illustrates the effect of prior infusion of AAP30 (SEQ ID NO:30) on amylin-induced hypocalcemia. Plasma calcium (mM)±SEM is plotted as a function of hours after start of amylin. Test animals were infused with a 1.5 mg bolus of AAP30 (SEQ ID NO:30), followed by an infusion of 3 mg/hr for a further 1.5 hours. At t=0 hours (0.5 hours after the start of the AAP30 (SEQ ID NO:30) infusion) a 50 μg bolus of amylin was administered followed by an infusion of 50 μg/hour which continued until the end of the experiment. Squares indicate the response when amylin is administered in the presence of AAP30 (SEQ ID NO:30), circles, when amylin is administered alone, and triangles, when saline is administered instead of amylin.
Figure 12:
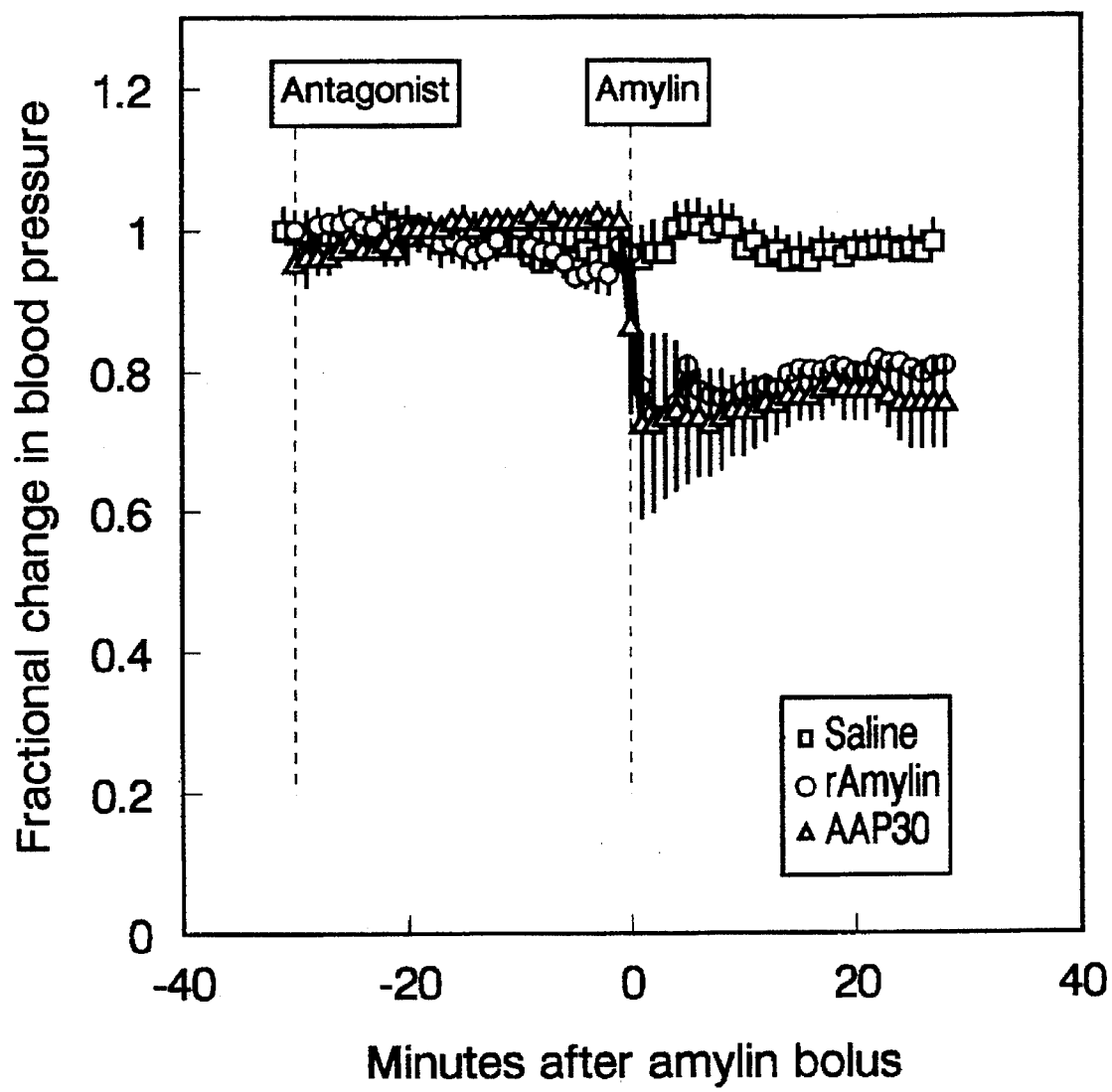
FIG. 12 illustrates the effect of prior infusion of AAP30 (SEQ ID NO:30) on amylin-induced hypotension. Fractional change in blood pressure (normalized so that blood pressure just before amylin administration=1.0)±SEM is plotted as a function of minutes after start of amylin. Test animals were infused with a 1.5 mg bolus of AAP30 (SEQ ID NO:30), followed by an infusion of 3 mg/hr for a further 1.5 hours. At t=0 hours (0.5 hours after the start of the AAP30 (SEQ ID NO:30) infusion) a 50 μg bolus of amylin was administered followed by an infusion of 50 μg/hour which continued until the end of the experiment. Triangles indicate the response when amylin is administered in the presence of AAP30 (SEQ ID NO:30), circles, when amylin is administered alone, and squares, when saline is administered instead of amylin.

Similarly, FIGS. 5–8 and 9–12, respectively, show the results of the evaluation of AAP30 (SEQ ID NO:30) and AAP37 (SEQ ID NO:37). AAP37 (SEQ ID NO:37) and AAP30 (SEQ ID NO:30) both suppressed the increases in plasma glucose (FIGS. 5 and 9, respectively) and plasma lactate (FIGS. 6 and 10, respectively) normally evoked by rat amylin. The results shown in FIGS. 7 and 11 illustrate that intravenous infusion of AAP37 (SEQ ID NO:37) and AAP30 (SEQ ID NO:30) into anesthetized rats did not inhibit the decreases in plasma calcium induced by rat amylin, i.e., that AAP37 (SEQ ID NO:37) and AAP30 (SEQ ID NO:30) are selective for the receptors that mediate the hyperglycemic and hyperlactemic actions of amylin relative to those receptors that mediate the hypocalcemic effect of amylin. The results shown in FIGS. 8 and 12 illustrate that AAP30 (SEQ ID NO:30) did not inhibit amylin-induced decreases in blood pressure, while AAP37 (SEQ ID NO:37) did block this effect. AAP37 (SEQ ID NO:37) blocked this effect, it is believed, because the Phe residue at the $R_3$ position of the peptide enables it to interact with CGRP receptors.

Example 11

Renin Studies With AAP40 (SEQ ID NO:40)

The amylin antagonist AAP40 (SEQ ID NO:40) was evaluated in vivo for its ability to inhibit amylin-induced plasma renin activity. Male Harlan Sprague Dawley (age 77–82 days, mass 300–350 g) fasted 18–20 hours were halothane anesthetized and cannulated as described in Example 10. One and a half hours after surgery, one treatment group of 7 rats was administered amylin as a 10 µg subcutaneous bolus (t=0). Another treatment group of 6 rats was similarly treated except that they were also administered AAP40 (SEQ ID NO:40) (1 mg/mL) as a primed continuous intravenous infusion of 0.5 mg, then 1.0 mg/hour for a further 1.5 hours (t=−10 min to t=+120 min). Blood samples were collected at t=−30, 0, 30, 60 and 120 min for assessment of plasma renin activity using the INCStar Gamma-Coat [$^{125}$I] plasma renin activity RIA kit (INCStar, Stillwater, Minn.; Cat. No. CA-533-553). Control rats, not administered AAP40 (SEQ ID NO:40), were injected with either saline or with primed/continuous amylin at t=0 hours, as described above.

Figure 13:
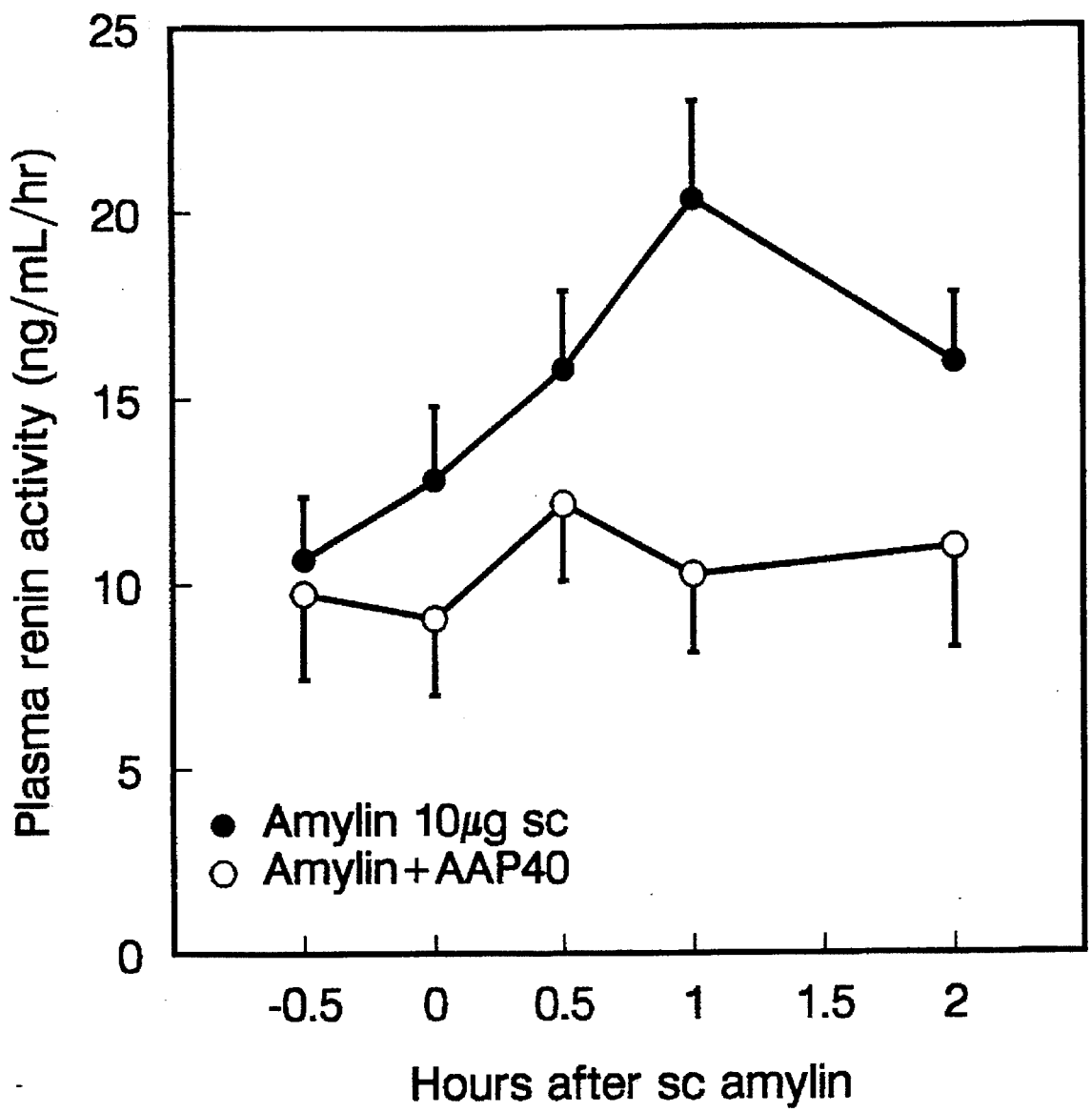
FIG. 13 illustrates the effect of prior infusion of APP40 (SEQ ID NO:40) on amylin-induced increases in plasma renin activity. Plasma renin activity is plotted as a function of hours after subcutaneous injection of 10 μg amylin. Test animals were given AAP40 (SEQ ID NO:40) (1 mg/mL) as a primed continuous infusion of 0.5 mg, then 1.0 mg/hr, beginning 10 minutes before amylin, for a further 1.5 hours. Circles indicate the response when amylin is administered in the presence of AAP40 (SEQ ID NO:40), filled circles, when amylin is administered alone.

FIG. 13 illustrates the results of this experiment. The data show that AAP40 (SEQ ID NO:40) effectively inhibits amylin-induced plasma renin activity in vivo.

---

I claim:

1. An amylin antagonist peptide having the formula:

$$X\text{-}R_1\text{ThrGlnR}_2\text{LeuAlaAsnR}_3\text{LeuValArgLeuGlnThrTyr-}$$
$$\text{ProArgThrAsnValGlyR}_4\text{AsnThrTyr—NH}_2$$

wherein $R_1$ is the amino acid residue Ala or a bond;

$R_2$ is an amino acid residue selected from the group consisting of Arg, Gln, Lys, Asn and Leu;

$R_3$ is an amino acid residue selected from the group consisting of Gln, Glu, Asn, Asp and Phe;

$R_4$ is an amino acid residue selected from the group consisting of Ala and Ser; and X is hydrogen or an acetyl group.

2. The amylin antagonist peptide according to claim 1 wherein $R_1$ is Ala, $R_2$ is Arg, $R_3$ is Glu, $R_4$ is Ser, and X is an acetyl group.

3. The amylin antagonist peptide according to claim 1 wherein $R_1$ is Ala, $R_2$ is Arg, $R_3$ is Gln, $R_4$ is Ser, and X is an acetyl group.

4. The amylin antagonist peptide according to claim 1 wherein $R_1$ is Ala, $R_2$ is Leu, $R_3$ is Glu, $R_4$ is Ser, and X is an acetyl group.

5. The amylin antagonist peptide according to claim 1 wherein $R_1$ is Ala, $R_2$ is Gln, $R_3$ is Glu, $R_4$ is Ser, and X is an acetyl group.

6. The amylin antagonist peptide according to claim 1 wherein $R_1$ is Ala, $R_2$ is Leu, $R_3$ is Gln, $R_4$ is Ser, and X is hydrogen.

7. The amylin antagonist peptide according to claim 1 wherein $R_1$ is Ala, $R_2$ is Gln, $R_3$ is Gln, $R_4$ is Ser, and X is hydrogen.

* * * * *